US010067331B2

(12) United States Patent
Okudaira et al.

(10) Patent No.: US 10,067,331 B2
(45) Date of Patent: Sep. 4, 2018

(54) STRUCTURED ILLUMINATION MICROSCOPE DEVICE

(71) Applicant: NIKON CORPORATION, Tokyo (JP)

(72) Inventors: Yosuke Okudaira, Konosu (JP); Hisao Osawa, Kashiwa (JP)

(73) Assignee: NIKON CORPORATION, Tokyo (JP)

( * ) Notice: Subject to any disclaimer, the term of this patent is extended or adjusted under 35 U.S.C. 154(b) by 154 days.

(21) Appl. No.: 15/093,177

(22) Filed: Apr. 7, 2016

(65) Prior Publication Data
US 2016/0216505 A1 Jul. 28, 2016

Related U.S. Application Data

(63) Continuation of application No. PCT/JP2014/005157, filed on Oct. 9, 2014.

(30) Foreign Application Priority Data

Oct. 9, 2013 (JP) .................................. 2013-211614

(51) Int. Cl.
*G02B 21/36* (2006.01)
*G02B 21/06* (2006.01)
(Continued)

(52) U.S. Cl.
CPC ......... *G02B 21/367* (2013.01); *G02B 5/1828* (2013.01); *G02B 21/008* (2013.01);
(Continued)

(58) Field of Classification Search
CPC .... G02B 21/06; G02B 27/58; G02B 21/0032; G02B 21/0056; G02B 21/365;
(Continued)

(56) References Cited

U.S. PATENT DOCUMENTS

RE38,307 E 11/2003 Gustafsson et al.
2009/0296205 A1* 12/2009 Ouchi ................... G02B 21/16
359/370
2015/0185463 A1 7/2015 Ohki et al.

FOREIGN PATENT DOCUMENTS

WO 2014/013720 A1 1/2014

OTHER PUBLICATIONS

Apr. 12, 2016 International Preliminary Report on Patentability issued in International Patent Application No. PCT/JP2014/005157.
(Continued)

*Primary Examiner* — Kim Vu
*Assistant Examiner* — Michael Vanchy, Jr.
(74) *Attorney, Agent, or Firm* — Oliff PLC

(57) ABSTRACT

A structured illumination microscope device includes acquisition unit that repeats a series of processing steps including controlling a combination of a wave vector and phase of fringes and acquiring N images; and computing unit in which processing for demodulating the image of the sample using a required M types of images from an image set of consecutive P images. The M types of images include: Q types (where Q≥3) of modulated images; and one type of modulated image having the wave vector in common with and the phase differing from at least one among the Q types of modulated images, or one unmodulated image.
An arrangement of the N images satisfies the uniformity condition, meaning "intensity distribution of the fringes is spatially uniform when accumulated between the N images" and the refresh condition, meaning "the M types of images are always included in the image set".

6 Claims, 28 Drawing Sheets

(51) Int. Cl.
  *G02B 5/18*    (2006.01)
  *H04N 5/225*   (2006.01)
  *G02B 21/00*   (2006.01)
  *G02B 27/58*   (2006.01)
  *G01N 21/64*   (2006.01)

(52) U.S. Cl.
  CPC ......... *G02B 21/0076* (2013.01); *G02B 21/06* (2013.01); *G02B 27/58* (2013.01); *H04N 5/2256* (2013.01); *G01N 21/648* (2013.01); *G01N 21/6458* (2013.01)

(58) Field of Classification Search
  CPC .............. G02B 21/0076; G02B 21/008; G02B 21/367; G02B 5/1828; G01N 21/956; G01N 21/6458; G01N 21/648; H04N 5/2256
  See application file for complete search history.

(56) References Cited

OTHER PUBLICATIONS

Jan. 13, 2015 International Search Report issued in International Patent Application No. PCT/JP2014/005157.

* cited by examiner

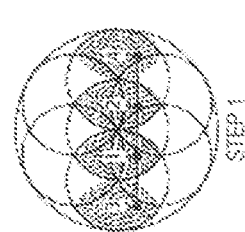
FIG. 21A
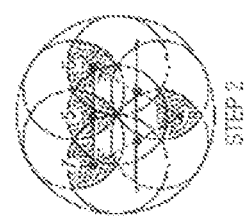
FIG. 21B
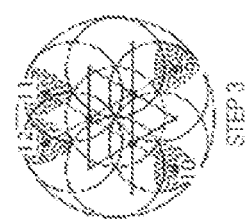
FIG. 21C
FIG. 21D

STRUCTURED ILLUMINATION MICROSCOPE DEVICE

CROSS REFERENCE TO THE RELATED APPLICATIONS

This application is a continuation application of International Application PCT/JP2014/005157, filed Oct. 9, 2014, designating the U.S., and claims the benefit of priority from Japanese Patent Application No. 2013-211614, filed on Oct. 9, 2013, the entire contents of which are incorporated herein by reference.

BACKGROUND

1. Field

The present invention relates to a structured illumination microscope device.

2. Description of the Related Art

A technique of modulating the spatial frequency of the structure of an object to be observed using illumination light is known as a technique for carrying out the super-resolution observation of an organism sample or other object to be observed (see Patent Literature 1: U.S. Reissue patent application Publication No. 38307).

In this technique, an object to be observed is irradiated with spatially-modulated illumination light, and high spatial frequency information surpassing the resolution limit contained in the structure of the object to be observed is made to contribute to image forming in a microscope optical system. Additionally, the spatial illumination phase is switched and calculations are performed on a plurality of modulated image data obtained under the different phases (hereinafter, referred to as "modulated image") in order to acquire demodulated image data (hereinafter, referred to as "demodulated image" or "super-resolution image").

However, observation at high speeds is difficult because, in order to observe one super-resolution image, it is necessary to acquire a plurality of modulated images and generate each spectrum of these modulated images.

As such, an object of the present invention is to optimize the demodulation processing required to acquire super-resolution images (demodulated images) from modulated images.

SUMMARY

One example of a structured illumination microscope device of the present invention includes acquisition unit that repeats a series of processing steps including controlling a combination of a wave vector and phase of fringes that spatially modulate a sample and sequentially acquiring N images related to the sample; and computing unit that performs demodulation of an image of the sample using a required M types of images from an image set of consecutive P images updated upon acquisition of L of the images on each of the image sets.

Note that the M types of images include the following images.

Q types (Q≥3) of modulated images having a mutually closed relationship between the wave vectors.
One type of modulated image having the wave vector in common with and the phase differing from at least one among the Q types of modulated images, or one unmodulated image.

Additionally, the arrangement of the N images fulfills the following conditions.

Uniformity condition: The intensity distribution of the fringes is spatially uniform when accumulated between the N images.
Refresh condition: The image set always includes the M types of images.

Another example of a structured illumination microscope device of the present invention includes a diffraction grating; a projection optical system that projects light from a light source onto an object to be observed via the diffraction grating or bypassing the diffraction grating; a control unit that controls a direction and a phase of the pattern of the diffraction grating; an image-forming optical system that forms an image of the object to be observed on which the pattern of the diffraction grating is projected; an image sensor that generates an image by capturing the image formed by the image-forming optical system; and computing unit that generates a super-resolution image of the object to be observed on the basis of at least one unmodulated image generated by the image sensor and an image generated by the image sensor on the basis of patterns in at least three directions of the diffraction grating. The control unit performs control such that a pattern in at least one direction of the diffraction grating is radiated uniformly on the object to be observed when a plurality of the super-resolution images is generated.

Another example of a structured illumination microscope device of the present invention includes a diffraction grating; a projection optical system that projects light from a light source onto an object to be observed via the diffraction grating or bypassing the diffraction grating; a control unit that controls a direction and a phase of a pattern of the diffraction grating; an image-forming optical system that forms an image of the object to be observed on which the pattern of the diffraction grating is projected; an image sensor that generates an image by capturing the image formed by the image-forming optical system; and computing unit that generates a super-resolution image of the object to be observed on the basis of an image generated by the image sensor on the basis of patterns in at least three directions of the diffraction grating. In cases where a pattern in at least one direction of the diffraction grating is not radiated uniformly on the object to be observed when the super-resolution image is generated, the control unit performs control such that a pattern in at least one direction of the diffraction grating is radiated uniformly on the object to be observed when a plurality of the super-resolution images is generated.

Yet another example of a structured illumination microscope device of the present invention includes a diffraction grating; a projection optical system that projects light from a light source onto an object to be observed via the diffraction grating or bypassing the diffraction grating; a control unit that controls a direction and a phase of a pattern of the diffraction grating; an image-forming optical system that forms an image of the object to be observed on which the pattern of the diffraction grating is projected; and an image sensor that generates an image by capturing the image formed by the image-forming optical system; and computing unit that generates a super-resolution image of the object to be observed on the basis of at least one unmodulated image generated by the image sensor and an image generated by the image sensor on the basis of patterns in at least three directions of the diffraction grating. The control unit changes the phase of a pattern in at least one direction of the diffraction grating when a plurality of the super-resolution images is generated.

Another example of a structured illumination microscope device of the present invention includes a diffraction grating; a projection optical system that projects light from a light source onto an object to be observed via the diffraction grating or bypassing the diffraction grating; a control unit that controls a direction and a phase of a pattern of the diffraction grating; an image-forming optical system that forms an image of the object to be observed on which the pattern of the diffraction grating is projected; and an image sensor that generates an image by capturing the image formed by the image-forming optical system; and computing unit that generates a super-resolution image of the object to be observed on the basis of an image generated by the image sensor on the basis of patterns in at least three directions of the diffraction grating. In cases where a pattern in at least one direction of the diffraction grating is not radiated uniformly on the object to be observed when the super-resolution image is generated, the control unit changes the phase of a pattern in at least one direction of the diffraction grating when a plurality of the super-resolution images is generated.

BRIEF DESCRIPTION OF DRAWINGS

FIGS. 21A to 21D are drawings explaining in detail Formula 1.33 of Section 1.6.

FIG. 27A is an xy cross-section and FIG. 28B is a zx cross-section.

FIGS. 28A and 28B are drawings illustrating the frequency range of a demodulated image in Section 2.4. FIG. 28A is an xy cross-section and FIG. 28B is a zx cross-section.

DETAILS DESCRIPTION OF THE EMBODIMENTS

Next, a structured illumination microscope device according to an embodiment of the present invention will be described.

<Explanation of the Device>

First, the configuration of the structured illumination microscope device will be described. The following description includes explanation of cases where the structured illumination microscope device is used as a total internal reflection fluorescence microscope (TIRFM).

Figure 1:
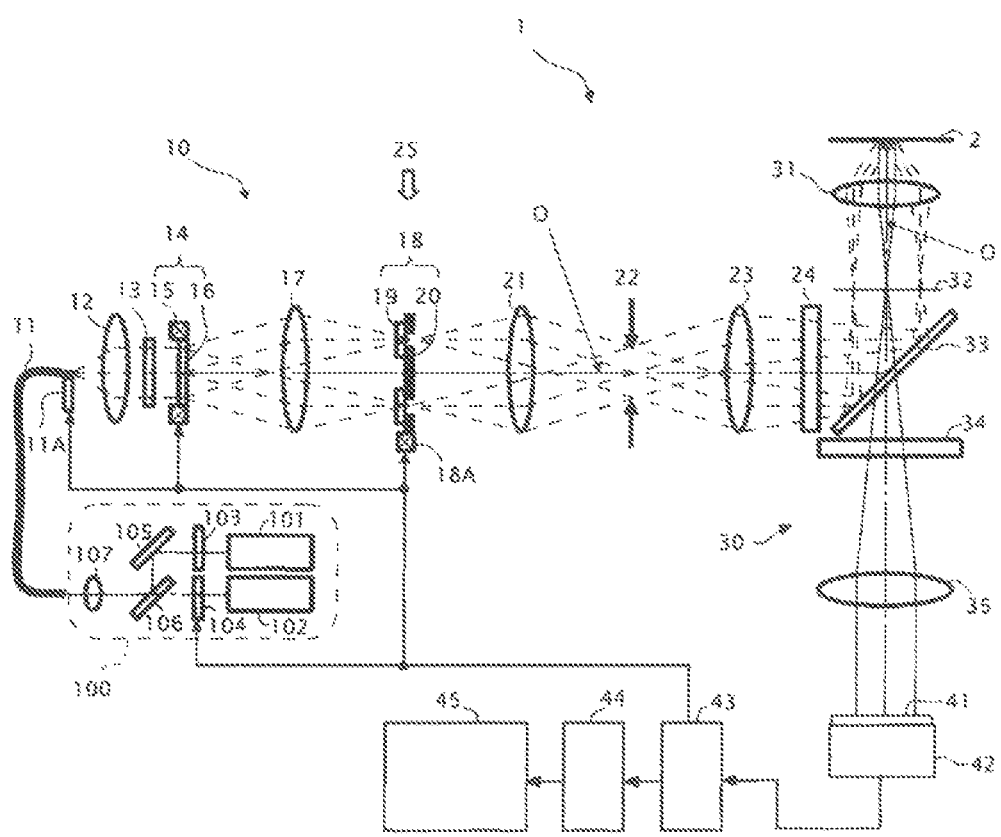
FIG. 1 illustrates the configuration of a structured illumination microscope device 1 according to Embodiment 1.

FIG. 1 illustrates the configuration of a structured illumination microscope device 1. As illustrated in FIG. 1, the structured illumination microscope device 1 includes a laser unit 100, an optical fiber 11, an illumination optical system 10, an imaging optical system 30, an image sensor 42, a control device 43, an image storage/processing device 44, and an image display device 45. The illumination optical system 10 is an epi-illumination optical system and illuminates a sample 2 using an objective lens 31 and a dichroic mirror 33 of the imaging optical system 30.

The laser unit 100 includes a first laser light source 101, a second laser light source 102, shutters 103 and 104, a mirror 105, a dichroic mirror 106, and a lens 107. The first laser light source 101 and the second laser light source 102 are both light sources that emit highly coherent laser light and emit different wavelengths of light. Here, assume that the wavelength $\lambda 1$ of the first laser light source 101 is greater than the wavelength $\lambda 2$ of the second laser light source 102 (that is, $\lambda 1 > \lambda 2$). The first laser light source 101, the second laser light source 102, and the shutters 103 and 104 are driven and controlled by the control device 43.

The optical fiber 11 is a polarization-maintaining single-mode fiber, for example, and guides laser light emitted from the laser unit 100. The position of the output end of the optical fiber 11 can be adjusted in the optical axis O direction by a position adjusting mechanism 11A. The position adjusting mechanism 11A is driven and controlled by the control device 43. The position adjusting mechanism 11A may be a piezo element or the like, for example.

The illumination optical system 10 includes, in order from the output end of the optical fiber 11, a collector lens 12, a polarizing plate 13, a light beam splitter 14, a condenser lens 17, a light beam selector 18, a lens 21, a field diaphragm 22, a field lens 23, an excitation filter 24, the dichroic mirror 33, and the objective lens 31.

Note that when a polarization-maintaining single-mode fiber is used for the optical fiber 11, the polarization plane of the laser light is maintained while traveling through the optical fiber 11, and therefore a polarizing plate 13 is not strictly required. However, including the polarizing plate 13 is effective in maintaining the quality of the polarized light in the laser light. In contrast, if a multi-mode fiber is used for the optical fiber 11, the polarizing plate 13 is always necessary.

The light beam splitter 14 includes a translation mechanism 15 and a diffractive optical element (a diffraction grating) 16. The light beam selector 18 includes a half-wave plate 19, a beam selection member 20, and a rotation mechanism 18A. The light beam splitter 14 and the light beam selector 18 are driven and controlled by the control device 43.

The imaging optical system 30 includes, in order from the sample 2, the objective lens 31, the dichroic mirror 33, a barrier filter 34, and a second objective lens 35.

The sample 2 is fluorescent cells (that is, cells stained using a fluorescent dye) arranged on the surface of a parallel plate glass or fluorescent living cells (that is, moving cells stained using a fluorescent dye) grown in a petri dish, for example. Each of these cells has both a first fluorescent region that is excited by the light of wavelength $\lambda 1$ and a second fluorescent region that is excited by the light of wavelength $\lambda 2$.

When the structured illumination microscope device 1 is used as a total internal reflection fluorescence microscope (TIRFM), the objective lens 31 is configured as a liquid immersion (such as an oil immersion) objective lens. In other words, an immersion liquid (oil), not illustrated in the drawings, is filled into the gap between the objective lens 31 and the glass on which the sample 2 is arranged.

The image sensor 42 is a two-dimensional image sensor such as a CCD or a CMOS sensor. The image sensor 42 is driven by the control device 43 and captures the image formed on the imaging surface 41 in order to generate an image. This image is then sent to the control device 43 and stored in the image storage/processing device 44. The frame period of the image sensor 42 (that is, the period at which imaging is repeated) is determined by the limiting factor among factors such as the imaging time of the image sensor 42 (that is, the time needed to store electric charges and read out those electric charges), the time needed to switch the direction of the interference fringes, and other required times.

The control device 43 controls the laser unit 100, the position adjusting mechanism 11A, the light beam splitter 14, the light beam selector 18, and the image sensor 42.

The image storage/processing device 44 processes the image sent via the control device 43, stores the processed image in an internal memory device (not illustrated in the drawings), and outputs the processed image to the image display device 45.

Next, the behavior of the laser light in the structured illumination microscope device 1 will be described.

The laser light of wavelength $\lambda 1$ (first laser light) emitted from the first laser light source 101 travels past the shutter 103 to the mirror 105, reflects off of the mirror 105, and continues to the dichroic mirror 106. Meanwhile, the laser light of wavelength $\lambda 2$ (second laser light) emitted from the second laser light source 102 travels past the shutter 104 to the dichroic mirror 106 and is combined with the first laser light. The first laser light and the second laser light emitted from the dichroic mirror 106 pass through the lens 107 and enter the input end of the optical fiber 11. Moreover, the control device 43 controls the laser unit 100 to switch the wavelength of the laser light that enters the input end of the optical fiber 11 (that is, the used wavelength $\lambda$) between the longer wavelength $\lambda 1$ and the shorter wavelength $\lambda 2$.

The laser light that enters the input end of the optical fiber 11 propagates through the optical fiber 11 and creates a point light source at the output end of the optical fiber 11. The laser light emitted from that point light source is converted to a parallel beam by the collector lens 12 and then travels through the polarizing plate 13 to the diffraction grating 16 of the light beam splitter 14, where the laser light is split into diffracted beams of various orders. These diffracted beams of various orders (hereinafter, referred to as "diffracted beam group" as needed) are focused by the condenser lens 17 on different positions on a pupil conjugate plane 25.

Here, the pupil conjugate plane 25 has a position conjugate to the pupil 32 of the objective lens 31 (the positions at which the ±first-order diffracted light is focused) via the lens 23 and the lens 21. The condenser lens 17 is arranged such that the focal point of the condenser lens 17 (the focal point on the downstream side) falls on the pupil conjugate plane 25. These conjugate positions are determined according to factors such as the aberration and vignetting of the objective lens 17, and the lenses 21 and 23 that must be considered by one of ordinary skill in the art during design.

The laser light emitted from the optical fiber 11 is typically linearly polarized light, and therefore the polarizing plate 13 can be removed. However, including the polarizing plate 13 is effective in reliably cutting out unneeded polarization components. Furthermore, it is preferable that the axis of the polarizing plate 13 be aligned with the polarization direction of the laser light emitted from the optical fiber 11 in order to increase the laser light utilization efficiency;

Next, the diffracted beams of each order traveling toward the pupil conjugate plane 25 enter the light beam selector 18 arranged near the pupil conjugate plane 25.

When the structured illumination microscope device 1 is used as a TIRFM, the light beam selector 18 selectively transmits only one pair of diffracted beams (here, the ±first-order diffracted beams) among the diffracted beams of each order incident on the light beam selector 18.

The ±first-order diffracted beams that pass through the light beam selector 18 are concentrated by the lens 21 on a plane near the field diaphragm 22 that is conjugate to the diffraction grating 16. Then, the ±first-order diffracted beams are converted to focused light by the field lens 23, pass through the excitation filter 24, reflect off of the dichroic mirror 33, and are focused at different positions on the pupil plane 32 of the objective lens 31.

The ±first-order diffracted beams that are concentrated on the pupil plane 32 are emitted from the end of the objective lens 31 as parallel beams and superposed on one another on the surface of the sample 2, forming interference fringes. These interference fringes are used as structured illumination light.

In order to satisfy this TIRE condition, the focused light spots formed by the ±first-order diffracted beams on the pupil plane 32 must be positioned in a prescribed circular band-shaped region positioned on the outermost periphery of the pupil plane 32. When this condition is satisfied, the interference fringes create an evanescent field near the surface of the sample 2.

When the sample 2 is illuminated with this structured illumination light, the difference between the periodic structure of the structured illumination light and the periodic structure of the sample 2 (that is, the periodic structure of the fluorescent regions) produces moire fringes. In the moire fringes, the high frequency structures of the sample 2 are shifted to frequencies lower than the original frequencies, and the light (fluorescent light) produced by these structures returns toward the objective lens 31 at angles smaller than the original angles. As a result, when the sample 2 is illuminated with the structured illumination light, even the high frequency structural information of the sample 2 (that is, the high frequency structural information of the fluorescent regions) is transmitted by the objective lens 31.

The fluorescent light produced by the sample 2 enters the objective lens 31 and is converted to parallel light by the objective lens 31. This light then proceeds through the dichroic mirror 33, the barrier filter 34, and the second objective lens 35 and forms a modulated image of the sample 2 on the imaging surface 41 of the image sensor 42.

This modulated image is translated into image data by the image sensor 42 and then sent to the control device 43 and stored in the image storage/processing device 44. Furthermore, the image storage/processing device 44 applies demodulation processing (described in more detail later) to the modulated images stored therein to generate a demodulated image (a super-resolution image). Furthermore, this super-resolution image is stored in the internal memory device (not illustrated in the drawings) of the image storage/processing device 44 and then sent to the image display device 45.

Next, the light beam splitter 14 will be described in detail.

Figure 2A:
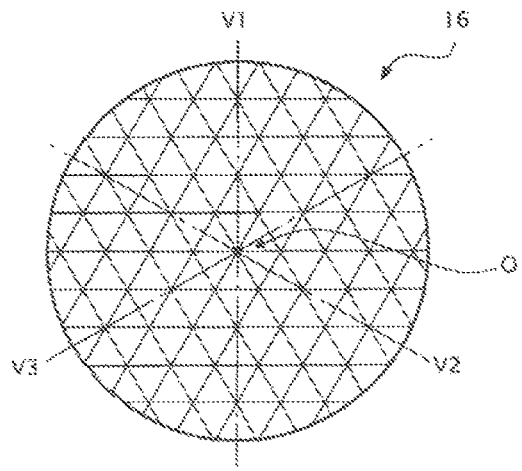
FIGS. 2A and 2B illustrate a light beam splitter 14.
Figure 2B:
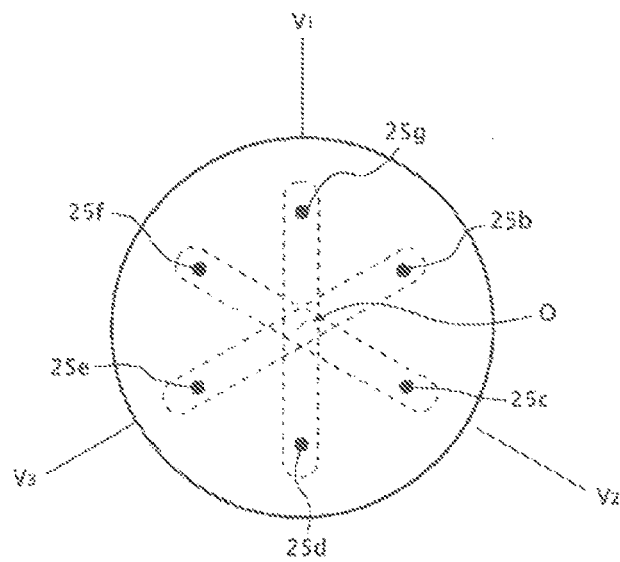

FIGS. 2A and 2B illustrate the light beam splitter 14. FIG. 2A illustrates the diffraction grating 16 of the light beam splitter 14 as viewed from the optical axis O direction, and FIG. 2B illustrates the positional relationship of the focused light spots formed on the pupil conjugate plane by the ±first-order diffracted beams. Note that FIG. 2A is only a schematic drawing, and the actual periodic structure of the diffraction grating 16 is not limited to the periodic structure illustrated in FIG. 2A.

As illustrated in FIG. 2A, the diffraction grating 16 is a two-dimensional diffraction grating with a periodic structure that extends in a plurality of different directions perpendicular to the optical axis O of the illumination optical system 10. Here, the diffraction grating 16 has a periodic structure that extends in a first direction V1, a second direction V2, and a third direction V3 which are offset by 120° from each other. It is assumed that the period (pitch) of the periodic structure of the diffraction grating 16 is the same in all three directions.

The periodic structure of the diffraction grating 16 may be a concentration-type periodic structure formed by taking advantage of concentration (transmittance) or a phase difference-type periodic structure formed by taking advantage of level differences (phase differences). However, it is preferable that the periodic structure be a phase difference-type periodic structure because this type of periodic structure exhibits higher diffraction efficiency of the ±first-order diffracted light.

The parallel beam that enters the diffraction grating 16 is converted into a first diffracted beam group split in the first direction V1, a second diffracted beam group split in the second direction V2, and a third diffracted beam group split in the third direction V3.

The first diffracted beam group contains a zero-order diffracted beam and ±first-order diffracted beams. Among these diffracted beams, the diffracted beams of the same order (that is, the ±first-order diffracted beams) proceed in directions symmetric about the optical axis O.

Likewise, the second diffracted beam group contains a zero-order diffracted beam and ±first-order diffracted beams. Among these diffracted beams, the diffracted beams of the same order (that is, the ±first-order diffracted beams) proceed in directions symmetric about the optical axis O.

Likewise, the third diffracted beam group contains a zero-order diffracted beam and ±first-order diffracted beams. Among these diffracted beams, the diffracted beams of the same order (that is, the ±first-order diffracted beams) proceed in directions symmetric about the optical axis O.

The ±first-order diffracted beams of the first diffracted beam group, the ±first-order diffracted beams of the second diffracted beam group, and the ±first-order diffracted beams of the third diffracted beam group are focused at different positions on the pupil conjugate plane by the condenser lens 17.

Furthermore, as illustrated in FIG. 2B, the focused light spots 25d and 25g formed by the ±first-order diffracted beams of the first diffracted beam group are symmetric about the optical axis O, and the direction in which the focused light spots 25d and 25g are arranged corresponds to the first direction V1.

Moreover, the focused light spots 25c and 25f formed by the ±first-order diffracted beams of the second diffracted beam group are symmetric about the optical axis O, and the direction in which the focused light spots 25c and 25f are arranged corresponds to the second direction V2. The distance from the focused light spots 25c and 25f of the second diffracted beam group to the optical axis O is the same as the distance from the focused light spots 25d and 25g of the first diffracted beam group to the optical axis O.

Furthermore, the focused light spots 25b and 25e formed by the ±first-order diffracted beams of the third diffracted beam group are symmetric about the optical axis O, and the direction in which the focused light spots 25b and 25e are arranged corresponds to the third direction V3. The distance from the focused light spots 25b and 25e of the third beam group to the optical axis O is the same as the distance from the focused light spots 25d and 25g of the first diffracted beam group to the optical axis O.

Here, the distance D from the optical axis O to the focused light spots 25b to 25g is given by the following formula, where $\lambda$ is the wavelength of the laser light emitted from the optical fiber 11, P is the pitch of the periodic structure of the diffraction grating 16, and fc is the focal length of the lens 17.

$$D \propto 2fc\lambda/P$$

Here, the term "focused light spots" refers to the weighted center positions of regions that have an intensity of at least 80% of the maximum intensity. Therefore, in the illumination optical system 10 of the present embodiment, the light beams do not necessarily have to be focused to the point of forming perfect focused light spots.

In the light beam splitter 14 described above, the translation mechanism 15 is a piezo motor or the like. The translation mechanism 15 moves the diffraction grating 16 in a direction that is orthogonal to the optical axis O of the illumination optical system 10 but not orthogonal to the first direction V1, the second direction V2, and the third direction V3. Moving the diffraction grating 16 in this direction shifts the phase of the fringes of the structured illumination light (this will be described in more detail later).

Next, the light beam selector 18 will be described in detail.

Figure 3A:
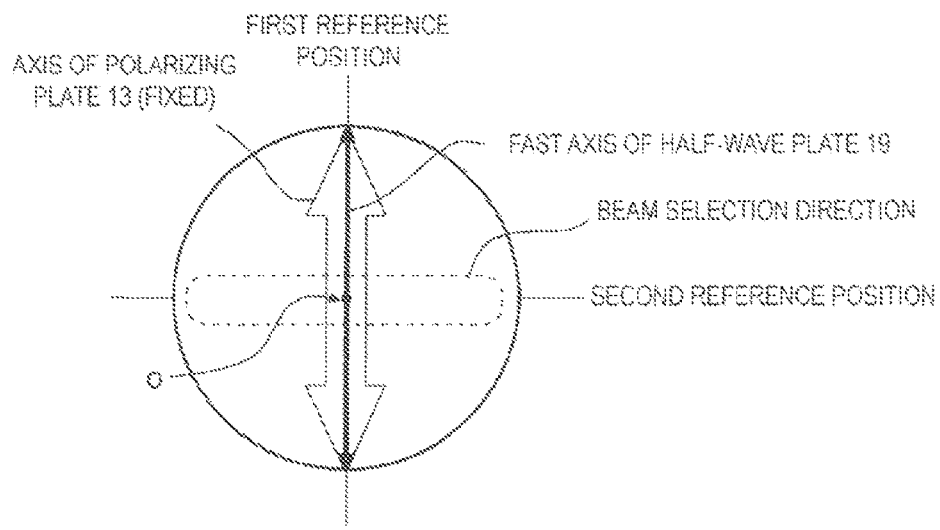
FIGS. 3A and 3B illustrate the function of a half-wave plate 19 of a light beam selector 18.
Figure 3B:
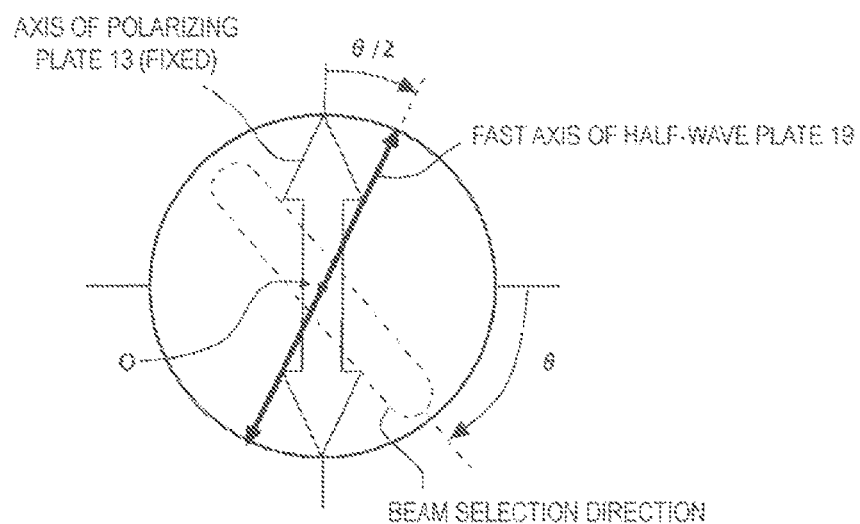
Figure 4A:
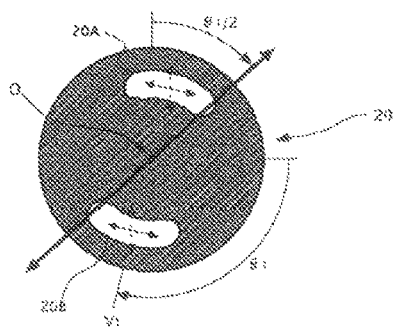
FIGS. 4A to 4C illustrate the function of a beam selection member 20 of the light beam selector 18.
Figure 4B:
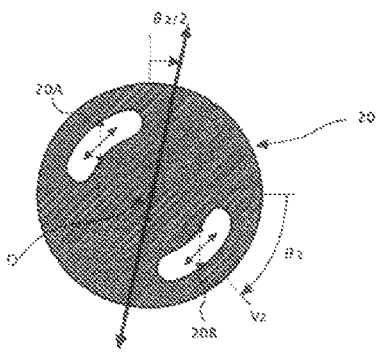
Figure 4C:
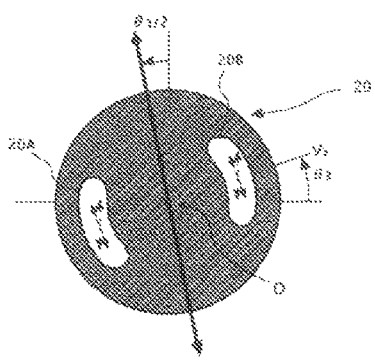

FIGS. 3A to 4C illustrate the light beam selector 18. As illustrated in FIGS. 3A and 3B, the half-wave plate 19 of the light beam selector 18 sets the polarization direction of the diffracted beams of each order incident thereon. As illustrated in FIGS. 4A to 4C, the beam selection member 20 of the light beam selector 18 is a mask that selectively transmits just the ±first-order diffracted beams of one group among the first to third diffracted beam groups.

The rotation mechanism (not illustrated in the drawings) of the light beam selector 18 rotates the beam selection member 20 about the optical axis O in order to switch ±first-order diffracted beams to be selected of the first to third diffracted beam groups. The rotation mechanism also rotates the half-wave plate 19 about the optical axis O in unison with the beam selection member 20 in order to keep the selected ±first-order diffracted beams that are incident on the sample 2 s-polarized.

In other words, the light beam selector 18 switches the direction of the structured illumination light fringes while maintaining the state of those structured illumination light fringes. Next, the conditions for maintaining the state of the fringes will be described in more detail.

First, the fast axis of the half-wave plate 19 must be oriented such that the polarization direction of ±first-order diffracted beams to be selected is orthogonal to the direction in which the ±first-order diffracted beams are split (one of the first direction V1 to third direction V3). Here, the "fast axis" of the half-wave plate 19 refers to the axis in the direction in which the phase delay of light polarized in that direction is minimized when that polarized light passes through the half-wave plate 19.

An opening pattern formed in the beam selection member 20 includes a first opening 20A and a second opening 20B that each allow one of the ±first-order diffracted beams of the same diffracted beam group to pass through. The lengths of the first opening 20A and the second opening 20B around the optical axis O are set to lengths that allow diffracted beams that are linearly polarized in the abovementioned direction to pass through. Therefore, the first opening 20A and the second opening 20B both have a partial ring shape.

Here, the rotation position of the half-wave plate 19 illustrated in FIG. 3A, in which the fast axis of the half-wave plate 19 is parallel to the axis of the polarizing plate 13, serves as a reference rotation position for the half-wave plate 19 (hereinafter, a "first reference position").

Furthermore, the rotation position of the beam selection member 20 in which the beam selection direction of the beam selection member 20 (that is, the direction in which ±first-order diffracted beams to be selected are split) is orthogonal to the axis of the polarizing plate 13 serves as a reference rotation position for the beam selection member 20 (hereinafter, a "second reference position").

As illustrated in FIG. 3B, the rotation of the half-wave plate 19 and the beam selection member 20 should be controlled such that the amount by which the half-wave plate 19 is rotated from the first reference position is equal to half of the amount by which the beam selection member 20 is rotated from the second reference position.

In other words, when the half-wave plate 19 is rotated by $\theta/2$ from the first reference position, the beam selection member 20 is rotated by $\theta$ from the second reference position.

Therefore, as illustrated in FIG. 4A, in order to select the ±first-order diffracted beams of the first diffracted beam group (that are split in the first direction V1), the rotation mechanism 18A of the light beam selector 18 rotates the beam selection member 20 clockwise such that the beam selection direction thereof is rotated by an angle of $\theta 1$ from the second reference position and also rotates the half-wave plate 19 clockwise such that the fast axis thereof is rotated by an angle of $\theta 1/2$ from the first reference position.

As illustrated by the dashed arrows in FIG. 4A, the polarization direction of the diffracted beams of each order before passing through the half-wave plate 19 are parallel to the axis of the polarizing plate 13. However, as illustrated by the solid arrows in FIG. 4A, the polarization direction of the diffracted beams of each order after passing through the half-wave plate 19 is rotated clockwise by an angle of $\theta 1$, and therefore the polarization direction of the selected ±first-order diffracted beams is orthogonal to the direction in which those ±first-order diffracted beams are split (the first direction V1).

Moreover, as illustrated in FIG. 4B, in order to select the ±first-order diffracted beams of the second diffracted beam group (that are split in the second direction V2), the rotation mechanism 18A of the light beam selector 18 rotates the beam selection member 20 clockwise such that the beam selection direction thereof is rotated by an angle of $\theta 2$ from the second reference position and also rotates the half-wave plate 19 clockwise such that the fast axis thereof is rotated by an angle of $\theta 2/2$ from the first reference position.

As illustrated by the dashed arrows in FIG. 4B, the polarization direction of the diffracted beams of each order before passing through the half-wave plate 19 are parallel to the axis of the polarizing plate 13. However, as illustrated by the solid arrows in FIG. 4B, the polarization direction of the diffracted beams of each order after passing through the half-wave plate 19 is rotated clockwise by an angle of $\theta 2$, and therefore the polarization direction of the selected ±first-order diffracted beams is orthogonal to the direction in which those ±first-order diffracted beams are split (the second direction V2).

Similarly, as illustrated in FIG. 4C, in order to select the ±first-order diffracted beams of the third diffracted beam group (that are split in the third direction V3), the rotation mechanism 18A of the light beam selector 18 rotates the beam selection member 20 counter-clockwise (as viewed from the sample side—the same applies below) such that the beam selection direction thereof is rotated by an angle of $\theta 3$ from the second reference position and also rotates the half-wave plate 19 counter-clockwise such that the fast axis thereof is rotated by an angle of $\theta 3/2$ from the first reference position.

As illustrated by the dashed arrows in FIG. 4C, the polarization direction of the diffracted beams of each order before passing through the half-wave plate 19 are parallel to the axis of the polarizing plate 13. However, as illustrated by the solid arrows in FIG. 4C, the polarization direction of the diffracted beams of each order after passing through the half-wave plate 19 is rotated counter-clockwise by an angle of $\theta 3$, and therefore the polarization direction of the selected ±first-order diffracted beams is orthogonal to the direction in which those ±first-order diffracted beams are split (the third direction V3).

In other words, the direction of the fast axis of the half-wave plate 19 is set according to the direction in which the ±first-order diffracted beams selected by the beam selection member 20 are split such that the fast axis of the half-wave plate 19 bisects the angle between the polarization direction of the ±first-order diffracted beams incident on the half-wave plate 19 (that is, the direction of the axis of the polarizing plate 13) and the polarization direction that the ±first-order diffracted beams should have after exiting from the half-wave plate 19 (that is, the direction orthogonal to the split direction).

Therefore, the rotation mechanism 18A of the light beam selector 18 should rotate the half-wave plate 19 and the beam selection member 20 at a gear ratio of 2:1.

The rotation mechanism 18A includes, for example, a support member (not illustrated in the drawings) that supports the beam selection member 20 and allows the beam selection member 20 to rotate about the optical axis O, a first gear (not illustrated in the drawings) formed surrounding the support member, a second gear (not illustrated in the drawings) that meshes with the first gear, and a motor (a rotation motor—not illustrated in the drawings) that is connected to the second gear. Activating this motor rotates the second gear, and this rotary force is transmitted to the first gear, thereby rotating the beam selection member 20 about the optical axis O.

Figure 5:
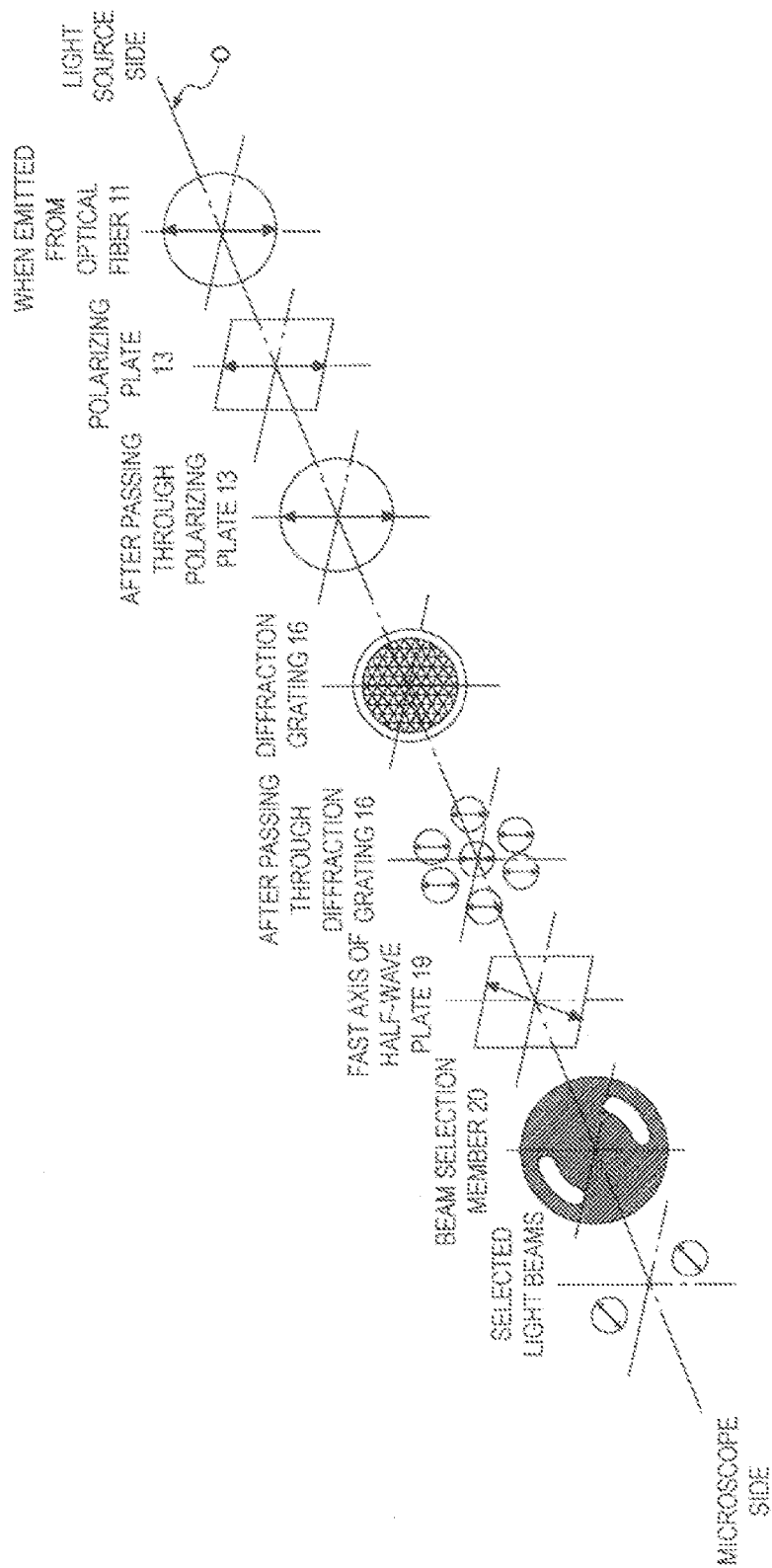
FIG. 5 illustrates the function of the light beam selector 18.

FIG. 5 illustrates the function of the light beam selector 18 as described above. In FIG. 5, the arrows surrounded by circles indicate the polarization direction of the light beams, and the arrows surrounded by squares indicate the direction in which the axis of an optical element is oriented.

In the description above, the rotatable half-wave plate 19 is used to keep the ±first-order diffracted beams incident on the sample 2 s-polarized. However, the rotatable half-wave plate 19 may be replaced by a fixed liquid crystal element that is used to achieve the same effect as the half-wave plate 19. Electronically controlling the orientation of the liquid crystal molecules in the liquid crystal element makes it possible to control the anisotropicity of the refractive index of the liquid crystal element, thereby making it possible to effectively rotate the fast axis of the half-wave plate about the optical axis O. There are also other ways of keeping the ±first-order diffracted beams incident on the sample 2 s-polarized.

Figure 6:
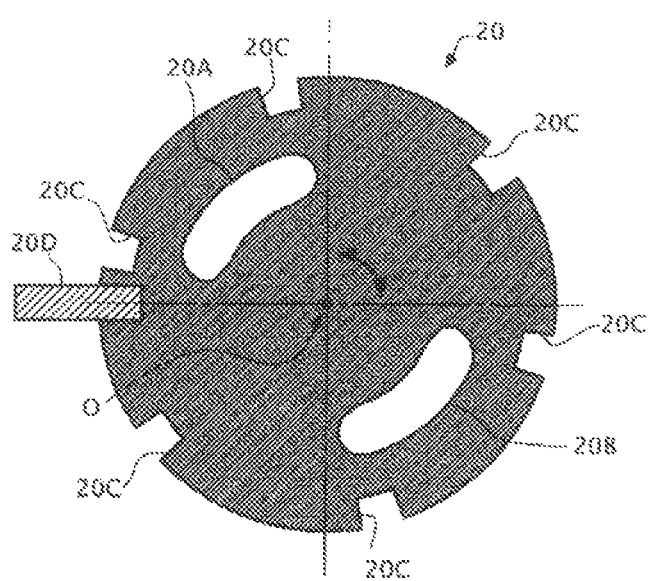
FIG. 6 illustrates a rotation mechanism 18A of the light beam selector 18.

Moreover, as illustrated in FIG. 6, a plurality of slits 20C (six slits in the example illustrated in FIG. 6) are formed in the periphery of the beam selection member 20, and the rotation mechanism 18A includes a timing sensor 20D for detecting the slits 20C. This makes it possible for the rotation mechanism 18A to detect not only the rotation angle of the light beam selector 18 but also the rotation angle of the half-wave plate 19.

Next, the translation mechanism 15 of the light beam splitter 14 will be described in detail.

Figure 7A:
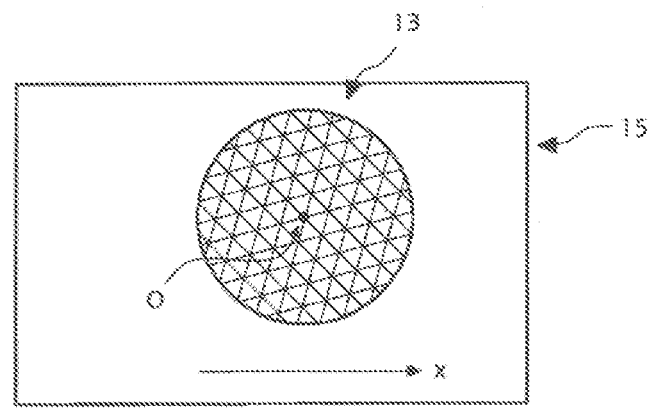
FIGS. 7A and 7B illustrate the operation of a translation mechanism 15 of the light beam splitter 14.
Figure 7B:
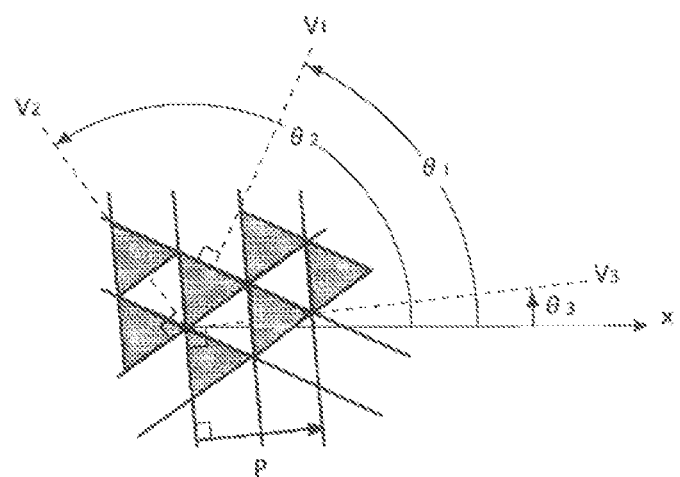

FIGS. 7A and 7B illustrate the operation of the translation mechanism 15 of the light beam splitter 14.

In order to be able to apply the demodulation processing (described in more detail later), at least two modulated images of the same sample 2 in which the directions of the interference fringes are the same but the phases thereof are different are required. This is because the modulated image of the structure of the sample 2 that is generated by the structured illumination microscope device 1 contains a zero-order modulation component, a +first-order modulation component, and a −first-order modulation component, which represent structural information in which the spatial frequency is modulated due to the structured illumination light. It is necessary to make these superposed three unknown parameters known during the demodulation processing (described in more detail later).

Therefore, as illustrated in FIG. 7A, the translation mechanism 15 of the light beam splitter 14 shifts the diffraction grating 16 in a direction (the x direction) that is orthogonal to the optical axis O of the illumination optical system 10 but not orthogonal to any of the first direction V1, the second direction V2, or the third direction V3 in order to shift the phase of the interference fringes.

However, the distance L by which the diffraction grating 16 must be shifted in order to shift the phase of the interference fringes by a desired amount φ is not necessarily the same when the beam selection direction of the light beam selector 18 is the first direction V1, when the beam selection direction is the second direction V2, and when the beam selection direction is the third direction V3.

As illustrated in FIG. 7B, let P be the pitch of the periodic structures of the diffraction grating 16 in the first direction V1, the second direction V2, and the third direction V3. Let θ1 be the angle between the direction in which the diffraction grating 16 is shifted (the x direction) and the first direction V1, let θ2 be the angle between the direction in which the diffraction grating 16 is shifted (the x direction) and the second direction V2, and let θ3 be the angle between the direction in which the diffraction grating 16 is shifted (the x direction) and the third direction V3. In this case, the distance L1 by which the diffraction grating 16 must be shifted in the x direction when the beam selection direction is the first direction V1 is $L1=\varphi \times P/(4\pi \times |\cos \theta 1|)$, the distance L2 by which the diffraction grating 16 must be shifted in the x direction when the beam selection direction is the second direction V2 is $L2=\varphi \times P/(4\pi \times |\cos \theta 2|)$, and the distance L3 by which the diffraction grating 16 must be shifted in the x direction when the beam selection direction is the third direction V3 is $L3=\varphi \times P/(4\pi \times |\cos \theta 3|)$.

In other words, the distance L by which the diffraction grating 16 must be shifted in the x direction to achieve a desired phase shift φ of the interference fringes depends on the angle θ between the beam selection direction (the first direction V1, the second direction V2, or the third direction V3) and the x direction, as given below by equation 1.

$$L=\varphi \times P/(a \times 4\pi \times |\cos \theta|) \tag{1}$$

The distance L by which the diffraction grating 16 must be shifted in the x direction to achieve a phase shift φ of 2π of the interference fringes is $P/(a \times 2 \times |\cos \theta|)$. This distance is equal to half of the pitch of the diffraction grating 16. In other words, shifting the diffraction grating 16 by a distance equal to half of the pitch thereof makes it possible to shift the phase of the structured illumination light by a full period (because the pitch of the interference fringes produced by the ±first-order diffracted light is equal to two times the pitch of the periodic structure of the diffraction grating 16).

However, a=1 (when M=1 or 2) and a=2 (when M=3). M is the number of directions of the periodic structure held by the diffraction grating 16.

<Description of Demodulation Process>

Demodulation processing by the image storage/processing device 44 will be described below.

The image storage/processing device 44 described above is constituted by a computer for performing computations by executing a computation program, a computation circuit for performing computation processing, or a combination of both. The computer may be a general purpose computer in which a computation program is installed via storage media or a communications network.

The basic procedures for demodulation processing by the image storage/processing device 44 will be described below. The basic procedures include the following four steps.

Step 1: Fourier-transform each of a plurality of modulated images and generate a plurality of spatial frequency spectra.

Step 2: In the Fourier space, isolate the zero-order modulation component of the fluorescence light, the +first-order modulation component of the fluorescence light, and the −first-order modulation component of the fluorescence light, which are superposed in each of the spatial frequency spectra.

Step 3: In the Fourier space, rearrange the isolated zero-order modulation component of the fluorescence light, the +first-order modulation component of the fluorescence light, and the −first-order modulation component of the fluorescence light, thereby generating the spatial frequency spectrum of the demodulated image.

Step 4: Inverse Fourier-transform the spatial frequency spectrum of the demodulated image, thereby acquiring the demodulated image (i.e. super-resolution image).

Note that two or more of these steps may be executed in a batch using a single arithmetic expression.

<Switching of 2D/3D>

Switching of 2D/3D of the structured illumination microscope device described above will be described below.

In the description above, the interference fringes projected onto the sample 2 are stipulated as two-beam interference fringes (that is, an example has been given where the structured illumination microscope device 1 is used in 2D-SIM mode), but three-beam interference fringes may also be used as the interference fringes projected onto the sample 2 (that is, the structured illumination microscope device 1 may be used in 3D-SIM mode).

Figure 8:
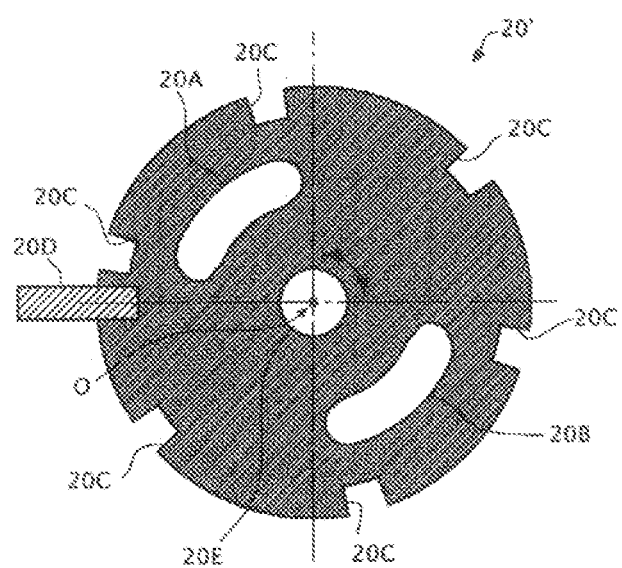
FIG. 8 illustrates a beam selection member 20' for a three-dimensional structured illumination microscopy (3D-SIM) mode.

For the 3D-SIM mode, the beam selection member 20' illustrated in FIG. 8 is used in place of the beam selection member 20 illustrated in FIG. 6. In this beam selection member 20', an additional opening 20E is formed in the beam selection member 20 illustrated in FIG. 6 in order to allow the zero-order diffracted beam to pass through. This opening 20E is formed near the optical axis O and is circular, for example. Using this type of beam selection member 20' makes it possible to use not only the ±first-order diffracted beams but also the zero-order diffracted beam to form interference fringes.

In this case, the interference fringes are produced by interference of three types of diffracted beams (three-beam interference) and spatially modulate the sample 2 not only in the surface direction but also in the depth direction of the sample 2. Therefore, these interference fringes can be used to produce a super-resolution image of the sample 2 in the depth direction thereof as well.

However, content of the demodulation processing to be executed by the image storage/processing device 44 differs between the 2D-SIM mode and the 3D-DIM mode. This is because in modulated images generated through 2D-SIM, three components, namely the zero-order modulation component of the fluorescence light, the +first-order modulation component of the fluorescence light, and the −first-order modulation component of the fluorescence light are superposed, but in modulated images generated through 3D-SIM, five components are superposed, namely the zero-order modulation component of the fluorescence light, the +first-order modulation component of the fluorescence light, the −first-order modulation component of the fluorescence light, the +second-order modulation component of the fluorescence light, and the −second-order modulation component of the fluorescence light.

Additionally, the number of frames that the control device 43 must acquire and the like differ because the number of superposed modulation components in modulated images differs between 2D-SIM mode and 3D-SIM mode. Next, the details of this configuration will be described.

<Additional Description of the Device>

In the device described above, the diffraction grating is shifted in order to shift the phase of the interference fringes, but instead of shifting the diffraction grating, the difference in optical path length between the ±first-order diffracted beams may be changed. In the case of changing the difference in optical path length, a phase plate may be inserted or removed from the optical path of the +first-order diffracted beam and/or the optical path of the −first-order diffracted beam.

However, because the relationship between the thickness of the phase plate and the amount of phase shift differs depending on the used wavelength, a plurality of phase plates having differing thicknesses may be mounted on a turret and be selectively inserted into the optical path in accordance with the used wavelength.

Additionally, when capturing the unmodulated image described later, the polarization direction may be set to any direction and may be changed during image capturing.

Additionally, in the device described above, the number of light source wavelengths is set to one, but may be expanded to two or more.

In the device described above, the half-wave plate that can be rotated about the optical axis O is used to keep the ±first-order diffracted beams incident on the sample 2 s-polarized. However, a fixed quarter-wave plate and a quarter-wave plate that can be rotated about the optical axis O may also be used. In this case, however, the rotation angle of the quarter-wave plate relative to the first reference position must be set to the same value as the rotation angle of the beam selection member relative to the second reference position.

Additionally, in the device described above, a combination of ±first-order diffracted light and zero-order diffracted light is used as the diffracted light for forming the interference fringes (two-beam interference fringes in 2D-SIM mode or three-beam interference fringes in 3D-SIM mode), but other combinations may also be used. In order to form the three-beam interference fringes, any three types of diffracted light in which there are equal intervals between the diffraction orders may be used. Therefore, combinations such as zero-order diffracted light, first-order diffracted light, and second-order diffracted light; ±second-order diffracted light and zero-order diffracted light; and ±third-order diffracted light and zero-order diffracted light may all be used, for example.

Furthermore, the illumination optical system 10 of the device described above is an epi-illumination optical system that uses the objective lens 31. However, the illumination optical system is not limited to this example and may be a transmission/reflection illumination optical system that uses a condenser lens in place of the objective lens 31. In this case, the focused light spots are formed on the pupil plane of the condenser lens.

<Section 1.1 (2D-SIM Premise)>

In this section, a 2D-SIM premise will be described.

Herein, interference fringe intensity distribution in 2D-SIM mode is defined as follows.

$I_0(x)$ is the fluorescent substance density of the sample and $K(x)$ is the interference fringe intensity distribution on the sample plane. It is assumed that the fluorescence light emitted by the sample is proportional to the illumination intensity. In such a case, the fluorescence light intensity distribution $I_{fl}(x)$ is expressed as follows.

$$I_{fl}(x)=I_o(x)K(x) \quad (1.1)$$

Additionally, because the fluorescence light emitted at each point of the sample is incoherent, an image captured by the objective lens according to the fluorescence light intensity distribution $I_{fl}(x)$, that is, the modulated image $I(x)$, is expressed by the following incoherent image forming formula.

$$I(x) = \iint dx' dy' PSF(x-x') I_{fl}(x') \quad (1.2)$$

Fourier transformations of each function are expressed below.

$$\tilde{I}(\xi) = \mathcal{F}[I(x)](\xi)$$

Here, the modulated image expressed in Fourier space (that is, the spatial frequency spectrum of the modulated image) is expressed below.

$$\tilde{I}(\xi) = OTF(\xi)\tilde{I}_{fl}(\xi) \quad (1.3)$$

Because OTF is zero when $|\xi|>2NA$, the spatial frequency spectrum of the modulated image is also zero when $|\xi|>2NA$. The following relationship is used here:

$$OTF(\xi) = \mathcal{F}[PSF(x)]$$

The fluorescence light intensity distribution in Fourier space is expressed as follows:

$$\tilde{I}_{fl}(\xi) = \iint d\xi' d\eta\, \tilde{I}_o(\xi-\xi')\tilde{K}(\xi') \quad (1.4)$$

Hereinafter, coefficients unnecessary to the description of the demodulation processing are omitted.

<Section 1.2 (Conventional 2D-SIM)>

In this section, demodulation processing in conventional 2D-SIM will be described for the purpose of comparison.

First, interference fringe intensity distribution in 2D-SIM is expressed as follows (the fringes have a sinusoidal intensity distribution).

$$K(x) = 1 + \cos\left(\frac{2\pi}{\lambda}\xi_0 \cdot x - \phi\right) \quad (1.5)$$

Where $\xi_0$ is the spatial frequency of the interference fringes (modulation frequency).

Thus, the interference fringe intensity distribution in Fourier space is expressed as follows:

$$\tilde{K}(\xi) = \delta(\xi) + \frac{\delta(\xi-\xi_0)e^{-i\phi} + \delta(\xi-\xi_0)e^{i\phi}}{2} \quad (1.6)$$

Note that $\xi$ indicates coordinates in Fourier space.

It is clear from the Formulas 1.6, 1.3, and 1.4 that the modulated image in Fourier space can be expressed as follows:

$$\tilde{I}(\xi) = OTF(\xi)(\tfrac{1}{2}e^{-i\varphi}\tilde{I}_o(\xi-\xi_0) + \tilde{I}_o(\xi) + \tfrac{1}{2}e^{i\varphi}\tilde{I}_o(\xi+\xi_0)) \quad (1.7)$$

Hereinafter, the spatial frequency spectrum in Fourier space is referred to simply as "spectrum". Additionally, when the phase of the interference fringes is $\varphi_i$, the acquired modulated image will be correspondingly marked with the subscript "$\varphi_i$".

Figure 9:
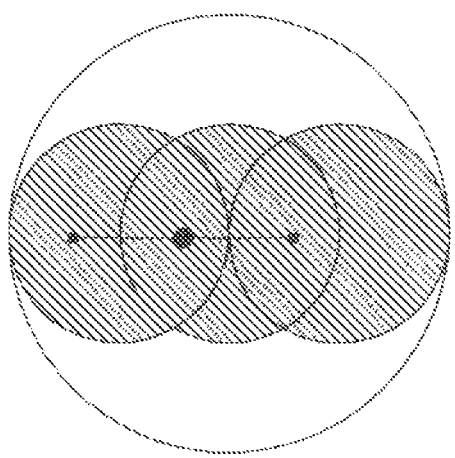
FIG. 9 is a diagram explaining the demodulation processing of a conventional two-dimensional structured illumination microscopy (2D-SIM) mode.

As described above, three components, namely the −first-order modulation component of the fluorescence light, the +first-order modulation component of the fluorescence light, and the zero-order modulation component of the fluorescence light, are superposed at the observation pointy in the spectrum of the modulated image acquired through 2D-SIM. The three terms on the right side of Formula 1.7 correspond to these three components. Specifically, because spatial modulation of the sample (fluorescence light) is carried out using fringes having a sine-wave intensity distribution, the spectrum of the modulated image can be expressed by the three modulation components of the fluorescence light (i.e. the zero-order modulation component and the ±first-order modulation components). The +first-order modulation component superposed at the observation point $\xi$ is a value (restoration value) that a restoration point ($\xi-\xi$) in the spectrum of the demodulated image must have; the −first-order modulation component superposed at the observation point $\xi$ is a value (restoration value) that a restoration point ($\xi+\xi_0$) in the spectrum of the demodulated image must have; and the zero-order modulation component superposed at the observation point $\xi$ is a value (restoration value) that a restoration point $\xi$ in the spectrum of the demodulated image must have. This applies to each observation point of the spectrum of the modulated image. The large black spot in FIG. 9 corresponds to an observation point and the two small black spots on either side of the large black spot and the large black spot itself correspond to the three restoration points restored from the observation point.

In the conventional 2D-SIM demodulation processing, in order to isolate each of the three modulation components superposed at each of the observation points in the spectrum of the modulated image, three equations are acquired by first acquiring three modulated images having fringes with differing phases, then generating a spectrum of each of the modulated images, and finally applying each of the spectra to the following three formulas (Formulas 1.8, 1.9, and 1.10, below). Conventionally, restoration values of the darkened regions in FIG. 9 (normal resolution range and super-resolution range) are found by solving these three formulas.

$$\tilde{I}_{\varphi 1}(\xi) = OTF(\xi)(\tfrac{1}{2}e^{-i\varphi_1}\tilde{I}_o(\xi-\xi_0) + \tilde{I}_o(\xi) + \tfrac{1}{2}e^{i\varphi_1}\tilde{I}_o(\xi+\xi_0)) \quad (1.8)$$

$$\tilde{I}_{\varphi 2}(\xi) = OTF(\xi)(\tfrac{1}{2}e^{-i\varphi_2}\tilde{I}_o(\xi-\xi_0) + \tilde{I}_o(\xi) + \tfrac{1}{2}e^{i\varphi_2}\tilde{I}_o(\xi+\xi_0)) \quad (1.9)$$

$$\tilde{I}_{\varphi 3}(\xi) = OTF(\xi)(\tfrac{1}{2}e^{-i\varphi_3}\tilde{I}_o(\xi-\xi_0) + \tilde{I}_o(\xi) + \tfrac{1}{2}e^{i\varphi_3}\tilde{I}_o(\xi+\xi_0)) \quad (1.10)$$

The formulas 1.8, 1.9, and 1.10 can be simplified by writing $OTF(\xi)$ as $\tau$.

$$\begin{bmatrix} \tilde{I}_{\phi_1}(\xi) \\ \tilde{I}_{\phi_2}(\xi) \\ \tilde{I}_{\phi_3}(\xi) \end{bmatrix} = \frac{\tau}{2} \begin{bmatrix} e^{-i\phi_1} & 2 & e^{i\phi_1} \\ e^{-i\phi_2} & 2 & e^{i\phi_2} \\ e^{-i\phi_3} & 2 & e^{i\phi_3} \end{bmatrix} \begin{bmatrix} \tilde{I}_o(\xi-\xi_0) \\ \tilde{I}_o(\xi) \\ \tilde{I}_o(\xi+\xi_0) \end{bmatrix} \quad (1.11)$$

So long as the determinant of matrix (hereinafter, "M") of this formula is not zero, the restoration values (right side) of the three restoration points corresponding to an observation point in the spectra of the three modulated images can be calculated from the three observation values (left side) of the observation point.

The spatial frequency (modulation frequency) of the fringes in conventional 2D-SIM is set such that the relationship $|\xi_0|<2NA$ is established, and the restoration value of the restoration point where $|\xi\pm\xi_0|>2NA$ can be found from the observation value obtained from the normal resolution region $|\xi|<2NA$. Thus, in conventional 2D-SIM, the restoration value outside the normal resolution region (i.e. the super-resolution region) can be restored, or, in other words, a super-resolution image can be obtained as the demodulated image.

The matrix M described above is not dependent on $\xi$. That is, the matrix M is not dependent on coordinates (i.e. spatial frequency) in Fourier space. Accordingly, FIG. 10 is the result of plotting the condition number of the matrix M with the phase $\varphi_i$ as a parameter.

Figure 10:
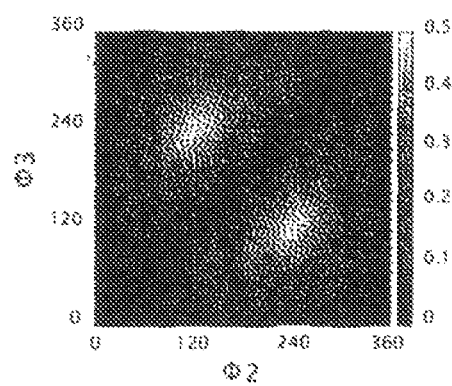
FIG. 10 is a distribution of the reciprocal of the condition number of the matrix M used in a conventional 2D-SIM.

FIG. 10 is a distribution of the reciprocal of the condition number of the matrix M. Here, however, the phase $\varphi_1$ of the first modulated image is set to 0°, and the phase $\varphi_2$ of the second modulated image and the phase $\varphi_3$ of the third modulated image are set as variables. In FIG. 10, the horizontal axis is $\varphi_2$ and the vertical axis is $\varphi_3$.

It is clear from FIG. 10 that when $\varphi_2=120°$ and $\varphi_3=240°$, conditions are optimal as the reciprocal of the condition number reaches a maximum value of 0.5. Accordingly, in conventional 2D-SIM, it is common practice to set the phase difference between the three frames to 120°.

<Section 1.3 (2D-SIM Two-Image Two-Point Restoration)>

In this section, "two-image two-point restoration" will be described as the 2D-SIM demodulation processing of the present embodiment. In this section, the control device 43 described above controls each constituent to acquire modulated images, and the image storage/processing device 44 executes the computations (the same holds true in other sections as well).

In this section, in the spectrum of one modulated image acquired through 2D-SIM, attention is called to the two observation points $\xi$ and $(\xi+\xi_0)$ separated from each other by the modulation frequency $\xi_0$ in the modulation direction, in which modulation components having a value in common are superposed.

Specifically, the −first-order modulation component of the fluorescence light superposed at the observation point $\xi$ and the zero-order modulation component of the fluorescence light superposed at the observation point $(\xi+\xi_0)$ both correspond to the restoration value of the restoration point $(\xi+\xi_0)$; and the +first-order modulation component of the fluorescence light superposed at the observation point $(\xi+\xi_0)$ and the zero-order modulation component of the fluorescence light superposed at the observation point $\xi$ both correspond to the restoration value of the restoration point $\xi$. That is, common restoration values of the two restoration points $\xi$ and $(\xi+\xi_0)$ are included in these two restoration points and $(\xi+\xi_0)$. This relationship will be used in the two-image two-point restoration discussed in this section. Hereinafter, a detailed description will be given.

First, if the interference fringe intensity distribution is assumed to be the same as in conventional 2D-SIM, the observation range of the spectrum of the modulated image is expressed as $|\xi|<2NA$.

The spatial frequency (modulation frequency) $\xi_0$ of the fringes in this section is set such that $|\xi|<2NA$ is established. Note that the spatial frequency (modulation frequency) $\xi_0$ of the fringes is set by the grating pitch (the pitch of fringes formed on the sample) of the diffraction grating 16.

In this case, the observation values of the two observation points $\xi$ and $(\xi+\xi_0)$, separated from each other by $\xi_0$, can be obtained from the spectrum of a single modulated image. However, the observation value of $(\xi+\xi_0)$ can only be obtained when $\xi$ is within a range where $(\xi+\xi_0)<2NA$ is satisfied.

The observation value of the observation point $\xi$ and the observation value of the observation point $(\xi+\xi_0)$ in the spectrum of the single modulated image are expressed in the following formulas.

$$\tilde{I}_\varphi(\xi)=OTF(\xi)(\tfrac{1}{2}e^{-i\varphi}\tilde{I}_o(\xi-\xi_0)+\tilde{I}_o(\xi)+\tilde{I}_o(\xi)+\tfrac{1}{2}e^{i\varphi}\tilde{I}_o(\xi+\xi_0)) \quad (1.12)$$

$$\tilde{I}_\varphi(\xi+\xi_0)=OTF(\xi+\xi_0)(\tfrac{1}{2}e^{-i\varphi}\tilde{I}_o(\xi)+\tilde{I}_o(\xi+\xi_0)+\tfrac{1}{2}e^{i\varphi}\tilde{I}_o(\xi+2\xi_0)) \quad (1.13)$$

Restoration values of four restoration points (unknowns) appear on the right side of Formulas 1.12 and 1.13. Two more formulas are needed to discover these four restoration values.

Accordingly, in this section, a total of four formulas which include the four restoration values (unknowns) are acquired by generating each spectrum of two modulated images having different phases $\varphi$, referencing a total of four observation values related to the two observation points $\xi$ and $(\xi+\xi_0)$, and applying these four observation values to Formulas 1.12 and 1.13.

To simplify the expressions, $\tau_1$ is substituted for $OTF(\xi)$, $\tau_2$ is substituted for $OTF(\xi+\xi_0)$, $\varphi_1$ represents the phase $\varphi$ of the first modulated image, and $\varphi_2$ represents the phase $\varphi$ of the second modulated image.

$$\begin{bmatrix} \tilde{I}_{\phi_1}(\xi) \\ \tilde{I}_{\phi_1}(\xi+\xi_0) \\ \tilde{I}_{\phi_2}(\xi) \\ \tilde{I}_{\phi_2}(\xi+\xi_0) \end{bmatrix} = \frac{1}{2}\begin{bmatrix} \tau_1 e^{-i\phi_1} & 2\tau_1 & \tau_1 e^{i\phi_1} & 0 \\ 0 & \tau_2 e^{-i\phi_1} & 2\tau_2 & \tau_2 e^{i\phi_1} \\ \tau_1 e^{-i\phi_2} & 2\tau_1 & \tau_1 e^{i\phi_2} & 0 \\ 0 & \tau_2 e^{-i\phi_2} & 2\tau_2 & \tau_2 e^{i\phi_2} \end{bmatrix} \quad (1.14)$$

Thus, in this section, so long as the determinant of matrix (hereinafter, "M") is not zero, the four restoration values (right side) can be calculated from the four observation values (left side) in the spectra of the two modulated images.

Figure 11:
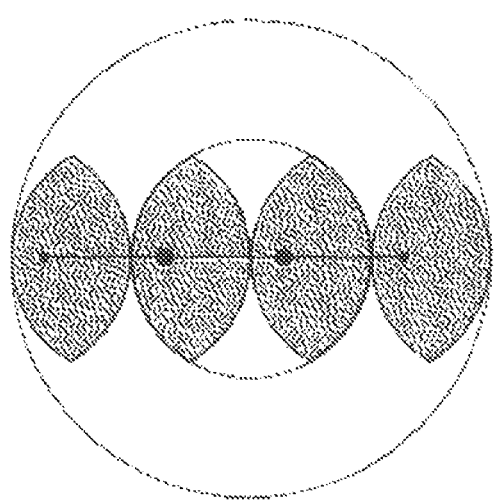
FIG. 11 is a diagram explaining the demodulation processing of Section 1.3.

In FIG. 11, the inner ring of the two rings shown is the outer edge ($|\xi|=2NA$) of the normal resolution range. The outer ring is the outer edge ($|\xi|=4NA$) of the super-resolution range.

The two large black spots in FIG. 11 represent two observation points separated from each other by the spatial frequency (modulation frequency) $\xi_0$ of the fringes; and the two large black spots and the two small black spots represent the four restoration points restored from the two observation points.

In this section, because the spectra of two modulated images with differing interference fringe phases are acquired, a total of four observation values is acquired from the two observation points in each of these two spectra. Moreover, the restoration value of each of these four restoration points can be found by applying these four observation values to Formula 1.14 described above.

In this section, by repeating the computation of the four restoration values while moving the two observation points within the normal resolution range, the restoration values of the entire darkened region in FIG. 11 can be found.

Accordingly, in this section, regardless of the number of acquired modulated images (the number of generated spectra) being two, restoration values of at least a portion of the normal resolution range and restoration values of at least a portion of the super-resolution range can be found.

<Section 1.3.1 (Restorability Conditions)>

In this section, the condition required for the demodulation processing of Section 1.3 will be described.

In order for Formula 1.14 to have a unique solution, the determinant of the matrix M must be a value other than zero. The determinant of the matrix M is expressed as follows:

$$\det M = \begin{bmatrix} \tau_1 e^{-i\phi_1} & 2\tau_1 & \tau_1 e^{i\phi_1} & 0 \\ 0 & \tau_2 e^{-i\phi_1} & 2\tau_2 & \tau_2 e^{i\phi_1} \\ \tau_1 e^{-i\phi_2} & 2\tau_1 & \tau_1 e^{i\phi_2} & 0 \\ 0 & \tau_2 e^{-i\phi_2} & 2\tau_2 & \tau_2 e^{i\phi_2} \end{bmatrix} \quad (1.15)$$

-continued $$= \tau_1^2 \tau_2^2 \begin{bmatrix} e^{-i\phi_1} & 2 & e^{i\phi_1} & 0 \\ 0 & e^{-i\phi_1} & 2 & e^{i\phi_1} \\ e^{-i\phi_2} & 2 & e^{i\phi_2} & 0 \\ 0 & e^{-i\phi_2} & 2 & e^{i\phi_2} \end{bmatrix} \quad (1.16)$$

$$= 4\tau_1^2 \tau_2^2 (\cos(\phi_1 - \phi_2) - 1)^2 \quad (1.17)$$

Thus, as long as the phase difference Δφ between the phase φ$_1$ of the first modulated image and the phase φ$_2$ of the second modulated image is such that Δφ≠0, detM≠0 will be established and Formula 1.14 will have a unique solution. As a result, it is clear that Δφ≠0 is a condition required for the demodulation processing of Section 1.3.

<Section 1.3.4 (Characteristics of Δφ=π)>

In this section, the characteristics of Δφ=π will be described.

When Δφ=π, the following formulas are established.

$$\tilde{I}_{\phi_1}(\xi) = \frac{\tau_1}{2} (\tilde{I}_o(\xi - \xi_0) + 2\tilde{I}_o(\xi) + \tilde{I}_o(\xi + \xi_0)) \quad (1.21)$$

$$\tilde{I}_{\phi_2}(\xi) = \frac{\tau_1}{2} (-\tilde{I}_o(\xi - \xi_0) + 2\tilde{I}_o(\xi) - \tilde{I}_o(\xi + \xi_0)) \quad (1.22)$$

In this case, the phases applied to $$\tilde{I}_o(\xi - \xi_0), \tilde{I}_o(\xi + \xi_0)$$

are equivalent, so $I_o(\xi)$ can easily be solved for, as:

$$\tilde{I}_o(\xi) = \frac{1}{2\tau_1} (\tilde{I}_{\phi_1}(\xi) + \tilde{I}_{\phi_2}(\xi)) \quad (1.23)$$

Accordingly, by setting Δφ=π, unrestorable regions in the normal resolution region can be eliminated.

Figures 12A, 12B:
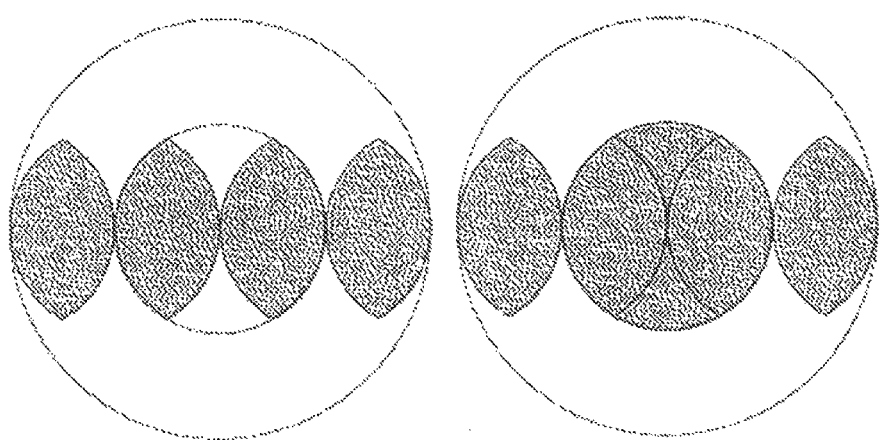
FIG. 12A illustrates a restorable range when $\Delta\varphi \neq \pi$ and FIG. 12B illustrates the restorable range when $\Delta\varphi = \pi$.

The darkened regions in FIG. 12A represent the restorable range when Δφ≠π, and the darkened regions in FIG. 12B represent the restorable range when Δφ=π (in both drawings, |ξ$_0$|=2NA). In FIGS. 12A and 12B, the inner ring of the two rings shown is the outer edge (|ξ|=2NA) of the normal resolution range, and the outer ring is the outer edge (|ξ|=4NA) of the super-resolution range.

Figure 13:
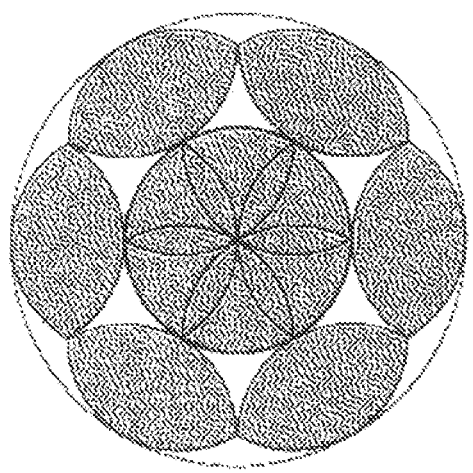
FIG. 13 illustrates a restorable range in a case where the number of directions of interference fringes in Section 1.3 is set to three.

Note that here, the number of directions of interference fringes is assumed to be one, but a wide region such as that illustrated in FIG. 13 can be restored by setting the number of directions of interference fringes to three and applying the demodulation processing in the same way as described in Section 1.3 to each direction.

<Section 1.4 (2D-SIM Two-Pass Restoration)>

In this section, "Two-pass restoration" will be described as the 2D-SIM demodulation processing of the present embodiment. In two-pass restoration, the number of directions of interference fringes is set to two.

Hereinafter, each of the interference fringes is expressed as a wave vector for the purpose of distinguishing the plurality of interference fringes with differing directions and periods (pitches). The magnitude of the wave vector represents the magnitude of the spatial frequency of the interference fringes, and the direction of the wave vector represents the direction of the interference fringes.

In this section, the following four steps are executed.

Step 1; The wave vector is ξ$_0$, two modulated images with differing phases are acquired, and spectra of each of the two modulated images are acquired. Each of the two modulated images is expressed as follows:

$$\{I_{\phi_1}^{(0)}, I_{\phi_2}^{(0)}\}$$

Figures 14A, 14B:
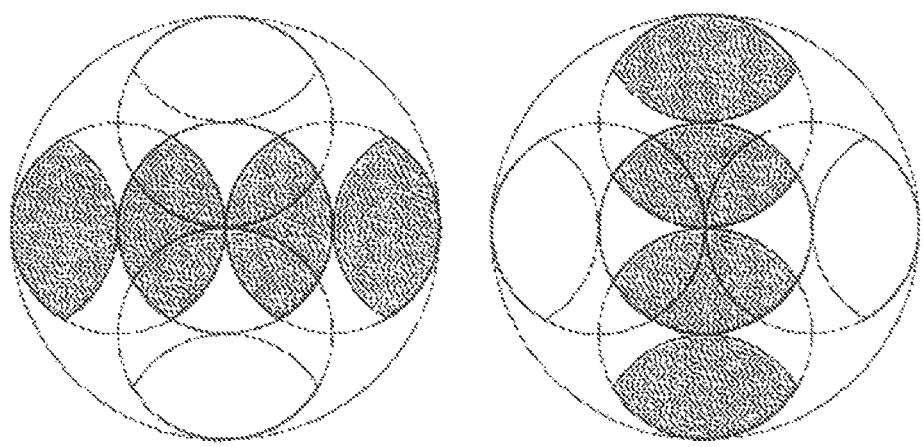
FIG. 14A illustrates a restorable region at the first step of Section 1.4
FIG. 14B illustrates a restorable region at the second step of Section 1.4.

Furthermore, by applying the same demodulation processing as that in Section 1.3 to the spectra of each of the two modulated images, the restoration value of the region illustrated in FIG. 14A is found.

Step 2: The wave vector is Fi, two modulated images with differing phases are acquired, and spectra of each of the two modulated images are acquired. Each of the two modulated images is expressed as follows:

$$\{I_{\phi_1}^{(1)}, I_{\phi_2}^{(1)}\}$$

Furthermore, by applying the same demodulation processing as that in Section 1.3 to the spectra of each of the two modulated images, the restoration value of the region illustrated in FIG. 14B is found.

Figures 15A, 15B:
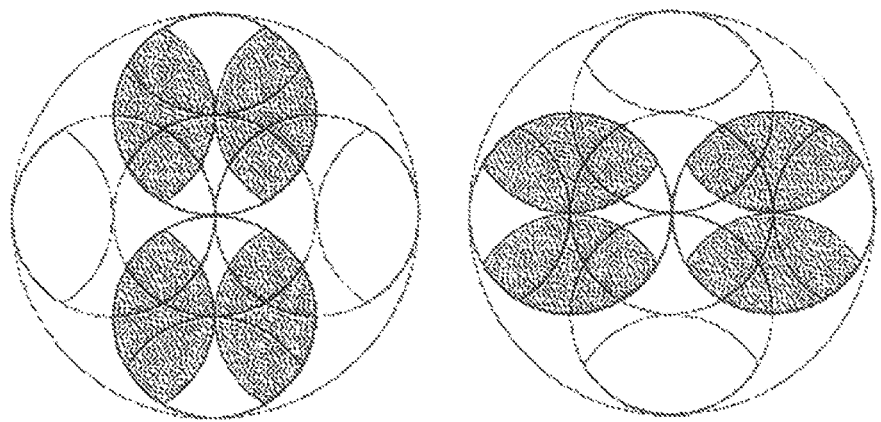
FIG. 15A illustrates a restorable region at the third step of Section 1.4
FIG. 15B illustrates a restorable region at the fourth step of Section 1.4.

Step 3: On the basis of the restoration values found in the preceding steps and the following formulas, the restoration values of the regions illustrated in FIG. 15A are found.

$$\tilde{I}_{\phi_1}^{(1)}(\xi) = \frac{\tau_1}{2} (e^{-i\phi_1} \tilde{I}_o(\xi - \xi_1) + 2\tilde{I}_o(\xi) + e^{i\phi_1} \tilde{I}_o(\xi + \xi_1)) \quad (1.24)$$

$$\tilde{I}_{\phi_2}^{(1)}(\xi) = \frac{\tau_1}{2} (e^{-i\phi_2} \tilde{I}_o(\xi - \xi_1) + 2\tilde{I}_o(\xi) + e^{i\phi_2} \tilde{I}_o(\xi + \xi_1)) \quad (1.25)$$

That is, by applying the restoration values found in the preceding steps, specifically:

$$\tilde{I}_o(\xi)$$

to Formula 1.26, the restoration values of the regions illustrated in FIG. 15A are found. Note that Formula 1.26 is a formula in which $$\tilde{I}_o(\xi - \xi_1), \tilde{I}_o(\xi + \xi_1)$$

are solved for Formulas 1.24 and 1.25.

$$\begin{bmatrix} \tilde{I}_o(\xi - \xi_1) \\ \tilde{I}_o(\xi + \xi_1) \end{bmatrix} = \frac{1}{2i\sin(\phi_1 - \phi_2)} \begin{bmatrix} e^{-i\phi_2} & -e^{i\phi_1} \\ -e^{i\phi_2} & e^{i\phi_1} \end{bmatrix} \begin{bmatrix} \frac{2}{\tau_1} \tilde{I}_{\phi_1}^{(1)}(\xi) - \tilde{I}_o(\xi) \\ \frac{2}{\tau_1} \tilde{I}_{\phi_2}^{(1)}(\xi) - \tilde{I}_o(\xi) \end{bmatrix} \quad (1.26)$$

However, in order for this step to be possible, Δφ≠πn (where n is an integer) must be true in at least step 2.

Step 4: On the basis of the restoration value of the normal resolution range found in step 2 (the |ξ|<2NA portion among the darkened regions in FIG. 14B), the restoration values of the regions illustrated in FIG. 15B are likewise found.

However, in order for this step to be possible, Δφ≠πn (where n is an integer) must be true in step 1.

Figure 16A:
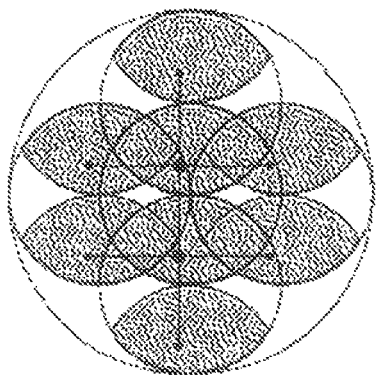
FIG. 16A is an explanatory drawing of Formula 1.27 of Section 1.4
Figure 16B:
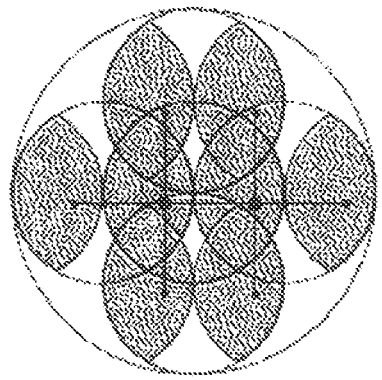
FIG. 16B is an explanatory drawing of a modified version of Formula 1.27.

Steps 1 and 3 can be combined and expressed as illustrated in FIG. 16B. That is, the four black spots linked in the horizontal direction on the horizontal line in FIG. 16B express the positions in Fourier space (wave number space) of the four restoration values (unknowns) found in the same system of equations as Formula 1.14, which is solved in step 1.

Among the three black spots linked in the vertical direction in each of the two vertical lines in FIG. 16B, the large black spot in the center represents the position in Fourier space (wave number space) of one known number found from the Formula of step 1; and the small black spots at both ends represent the positions in Fourier space (wave number space) of two restoration values (unknowns) of the system of equations 1.26, which is solved in step 3.

The relative positional relationships of these eight black spots is the same in every example. The range of possible positions in Fourier space (wave number space) of the black spots is restricted by the range of possible positions in Fourier space (wave number space) of the two large black spots (center black spots). Because the range of possible positions of the two large black spots is $|\xi|<2NA$, the range of positions of the restoration values (unknowns) that can be found through the calculations in steps 1 and 3 is the range of the darkened regions illustrated in FIG. 16B.

Note that FIG. 16A illustrates steps 2 and 4 in the same manner as FIG. 16B.

Figure 17:
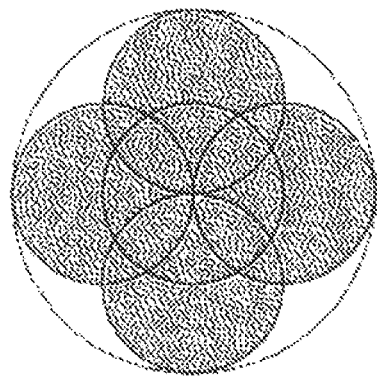
FIG. 17 illustrates the demodulated region according to a first example of Section 1.5.

Accordingly, in this section, the entire darkened region illustrated in FIG. 17 can be restored.

<Section 1.5 (2D-SIM Super-Resolution Example)>

In this section, two examples of super-resolution based on the results of the preceding sections will be described.

First, in a first example, Two-pass restoration is carried out, paying particular attention to curbing the number of modulated images (the number of spectra). Specifically, in the first example, the number of directions of the wave vector is set to two, two modulated images having differing phases are acquired at each of the two differing wave vectors $\xi_1$ and $\xi_2$ (a total of four modulated images are acquired), and the spectrum of each of these four modulated images is generated (a total of four spectra are generated). Moreover, to make Two-pass restoration possible, the phase difference $\Delta\varphi$ between the two modulated images acquired at the same wave vector is set to $\Delta\varphi \#7$. Additionally, the magnitude $\xi_i$ of the wave vector is set to $|\xi_i|=2NA$ (where i=1 or 2). In this case, the darkened region illustrated in FIG. 17 is restored.

Figure 18:
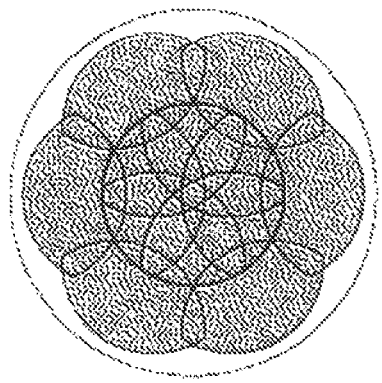
FIG. 18 illustrates the restored region according to a second example of Section 1.5.

Next, in a second example, "two-image two-point restoration" is performed instead of Two-pass restoration, paying particular attention to computation accuracy. Specifically, in the second example, the number of directions of wave vector is set to three, two modulated images having differing phases are acquired at each of the three differing wave vectors $\xi_1$, $\xi_2$, and $\xi_3$ (a total of six modulated images are acquired), and the spectrum of each of these six modulated images is generated (a total of six spectra are generated). Moreover, the phase difference $\Delta\varphi$ between the two modulated images acquired at the same wave vector is set to $\Delta\varphi \neq \pi$. Additionally, $|\xi_i|$ is intentionally set to be less than 2NA in order to avoid the formation of gaps in the restoration region. Specifically, the magnitude $|\xi_i|$ of the wave vector is set to $|\xi_i|=(\sqrt{3})\times NA$ (where i=1 or 2) in order to maximize IV within the range where gaps are not formed in the restoration region. In this case, the region illustrated in FIG. 18 is restored.

<Section 1.6 (2D-SIM Four-Image Three-Point Restoration)>

In this section, "four-image three-point restoration" will be described as the 2D-SIM demodulation processing of the present embodiment.

In this section, the number of directions of wave vectors is set to three (a modulated image is acquired at each of the three wave vectors $\xi_1$, $\xi_2$, and $\xi_3$ and a spectrum of each of these modulated images is generated).

Additionally, a closed relationship ($\xi_3=\xi_1-\xi_2$) is set for the three wave vectors $\xi 1$, $\xi_2$, and $\xi_3$.

Moreover, the number of phases is set to two (two modulated images $I^{(0)}$ and $I^{(1)}$ with the same fringe direction and differing phases are obtained) at one direction among the three directions (wave vector $\xi_1$), but at each of the other directions (wave vectors $\xi_2$ and $\xi_3$), the number of phases is held to one (two modulated images $I^{(2)}$ and $I^{(3)}$ with differing fringe directions are obtained).

Additionally, the phase difference $\Delta\varphi$ between the two modulated images having the same fringe direction is set to $\Delta\varphi=\pi$.

Additionally, in this section, the magnitude of each of the wave vectors is set to $|\xi_i|=2NA$ (where i=1, 2, or 3).

Here, the interference fringe intensity distribution of each of the four modulated images $I^{(0)}$, $I^{(1)}$, $I^{(2)}$, and $I^{(3)}$ are expressed as follows:

$$K^{(0)} = 1 + \cos\left(\frac{2\pi}{\lambda}\xi_1 \cdot x + \phi_0\right) \quad (1.29)$$

$$K^{(1)} = 1 + \cos\left(\frac{2\pi}{\lambda}\xi_1 \cdot x + \phi_1\right) \quad (1.30)$$

$$K^{(2)} = 1 + \cos\left(\frac{2\pi}{\lambda}\xi_2 \cdot x + \phi_2\right) \quad (1.31)$$

$$K^{(3)} = 1 + \cos\left(\frac{2\pi}{\lambda}(\xi_1 - \xi_2) \cdot x + \phi_3\right) \quad (1.32)$$

Here, assuming that the three wave vectors $\xi_1$, $\xi_2$, and $\xi_3$ form a triangle in the spectrum of each of the four modulated images $I^{(0)}$, $I^{(1)}$, $I^{(2)}$, and $I^{(3)}$, attention is called to the three observation points $\xi$, ($\xi+\xi_1$), and ($\xi+\xi_2$) positioned at the peaks (large black spots) of the triangle.

Because a total of 12 observation values are obtained from the three observation points $\xi$, ($\xi+\xi_1$), and ($\xi+\xi_2$) in each spectrum of the four modulated images $I^{(0)}$, $I^{(1)}$, $I^{(2)}$, and $I^{(3)}$, formulas equivalent to 12 of the formulas 1.7, corresponding to these 12 observation values, can be acquired. In this section, the following conditions are required to solve the system of equations constituted from these 12 formulas.

$$\cos(\varphi_0-\varphi_1) \neq 1 \quad (1.40)$$

$$\cos(\varphi_0-\varphi_2-\varphi_3) \neq \cos(\varphi_1-\varphi_2-\varphi_3) \quad (1.41)$$

Figure 19A:
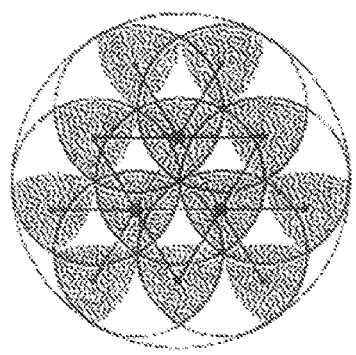
FIGS. 19A and B are explanatory drawings of Formula 1.33 in Section 1.6.

FIGS. 19A and B are explanatory drawings of the calculations. Note that $|\xi 1|=|\xi 2|$ and $\xi 1 \cdot \xi 2=|\xi 1||\xi 2|/2$.

The three large black spots in FIG. 19A represent the three observation points positioned at the peaks of the triangle formed from the three wave vectors $\xi_1$, $\xi_2$, and $\xi_3$ in the spectrum of each of the modulated images; and the three large black spots and the nine small black spots represent the restoration points (total of 12 restoration points) restored from these three observation points.

As described above, in this section, because the number of modulated images (the number of spectra) is set to four, a total of 12 observation values are acquired from three observation points. Restoration values of the 12 restoration points can be individually found by simultaneously solving the 12 formulas related to these 12 observation values.

In this section, by repeating the computation of the 12 restoration values while moving the three observation points, the restoration value of the entire darkened region in FIG. 19A can be found.

Figure 19B:
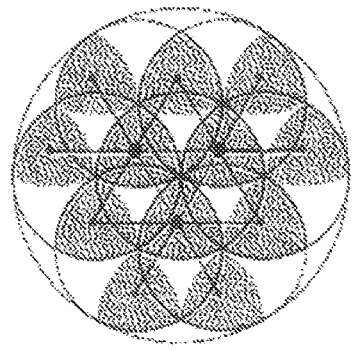

FIG. 19B is an explanatory drawing of a case where the direction of the triangle is inverted and restoration is performed as described above. It is possible to perform the restoration illustrated in FIG. 19A and the restoration illustrated in FIG. 19B in parallel. In this section, both restorations are performed and the entire darkened region illustrated in FIG. 20 is restored.

Figure 20:
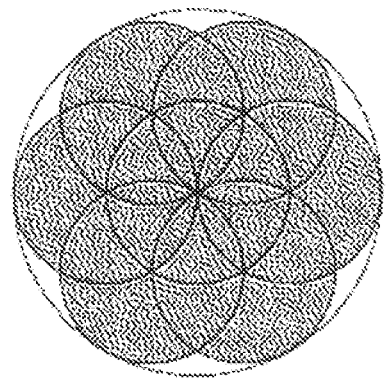
FIG. 20 illustrates the region to be restored in Section 1.6.

FIG. 20 is a drawing in which the restoration region illustrated in FIG. 19A and the restoration region illustrated in FIG. 19B are combined.

Hereinafter, a detailed description of an example of the calculation used to solve the system of equations constituted by the 12 formulas described in this section is given.

FIG. 21A to D are explanatory drawings that break the calculation used in this section down into three steps.

FIG. 21A illustrates the four restoration points 1 to 4 restored in step 1.

FIG. 21B illustrates the four restoration points 5 to 8 restored in step 2.

FIG. 21C illustrates the four restoration points 9 to 12 restored in step 3.

FIG. 21D is a correspondence table showing the relationship between the numbers 1 to 12 in the drawings and the restoration values.

Step 1: Restoration values of each of the restoration points 1, 2, 3, and 4 are found by applying the four observation values related to the two lined up observation points 1 and 2 at an interval $|\xi_1|$ in the direction of the wave vector $\xi_1$ to the two-image two-point restoration formula.

Step 2: Using the restoration values of each of the restoration points 1 and 2, restoration values of each of the four restoration points 5, 6, 7, and 8, separated from the restoration points 1 and 2 by the amount of the wave vectors $\xi_2$ and $\xi_3$, are found. Four formulas are used here, namely two formulas related to the direction of the wave vector $\xi_1$ (part for 2 phases), one formula related to the direction of the wave vector $\xi_2$, and one formula related to the direction of the wave vector $\xi_3$.

Step 3: Using the restoration values of each of the restoration points 1, 2, and 5, restoration values of each of the remaining restoration points 9, 10, 11, and 12, separated from the restoration points 1, 2, and 5 by the amount of the wave vectors $\xi_2$ and $\xi_3$, are found. Four formulas are used here, namely two formulas related to the direction of the wave vector (part for two observation points), and two formulas related to the direction of the wave vector $\xi_3$ (part for two observation points).

Of course, the method of solving the system of equations constituted by the 12 formulas described in this section is not limited to the procedure described above.

<Section 1.7 (Variation of 2D-SIM Four-Image Three-Point Restoration)>

In this section, a variation of four-image three-point restoration will be described.

In this section, the number of phases of all three directions are curbed to one and, instead, a single unmodulated image is acquired and the spectrum of that unmodulated image is generated.

The unmodulated image is an image acquired where $K^{(0)}=1$ and, for example, can be acquired in a state where the diffraction grating 16 and the light beam selector 18 described above are removed from the optical path. Additionally, the spectrum of the unmodulated image is obtained by Fourier transforming the unmodulated image.

As described above, in this section, because the number of modulated images (the number of spectra of the modulated images) is set to three and the number of unmodulated images (the number of spectra of the unmodulated images) is set to one, a total of 12 observation values are acquired from three observation points. Restoration values of the 12 restoration points can be individually found by simultaneously solving the 12 formulas (the nine in Formula 1.7 related to the spectrum of the modulated image, and the three in Formula 1.53 related to the spectrum of the unmodulated image) related to these 12 observation values.

Note that in this section, the following conditions are required.

$$\cos(\varphi_1-\varphi_2-\varphi_3)\neq 0 \tag{1.52}$$

$$I^{(0)}=OTF(\xi)I_o(\xi) \tag{1.53}$$

<Section 1.9 (2D-SIM Simultaneous Three-Direction Four-Image Three-Point Restoration)>

In this section, "simultaneous three-direction four-image three-point restoration" will be described as a variation of four-image three-point restoration.

First, in this section, as shown below, the interference fringes projected on the sample are the combined sum of three interference fringes having differing directions (three-direction interference fringes). Note that the method of projecting the three-direction interference fringes is described later.

$$K(x) = 1 + 2a\sum_{i=1}^{3}\cos\left(\frac{2\pi}{\lambda}\xi_i \cdot x + \phi_i\right) \tag{1.59}$$

That is, in this section, three-direction interference fringes simultaneously comprising the three wave vectors $\xi_1$, $\xi_2$, and $\xi_3$ are used, four modulated images having differing phases are acquired using the three-direction interference fringes, and a spectrum of each of these four modulated images is generated.

Note that $|\xi_i|\leq 2NA$ (where i=1, 2, or 3) and the three wave vectors $\xi_1$, $\xi_2$, and $\xi_3$ have a closed relationship ($\xi_3=\xi_1-\xi_2$).

Additionally, the value of "a" which specifies the amplitude of the three-direction interference fringes is selected so as to satisfy the following formula.

$$K(x)\geq 0, \forall x$$

First, a total of seven restoration values of restoration points are superposed at an observation point $\xi$ in the spectrum of the single modulated image acquired in this section, namely, restoration values attributed to the restoration point $\xi$ in the spectrum of the demodulated image, and restoration values ($\xi\pm\xi_i$) attributed to the restoration points (where i=1, 2, or 3) in the spectrum of the demodulated image.

In other words, a total of seven components are superposed at the observation point $\xi$ in the spectrum of the modulated image, namely, the zero-order modulation component of the fluorescence light, the ±first-order modulation components of the fluorescence light of the wave vector $\xi_1$, the ±first-order modulation components of the fluorescence light of the wave vector $\xi_2$, and the ±first-order modulation components of the fluorescence light of the wave vector $\xi_3$.

Here, assuming that the three wave vectors $\xi_1$, $\xi_2$, and $\xi_3$ form a triangle in the spectrum of each of the modulated images, attention is called to the three observation points $\xi_1(\xi+\downarrow_1)$, and ($\xi+\xi_2$) positioned at the peaks of the triangle.

The restoration values of the 12 restoration points are contained within the entirety of these three observation points $\xi$, ($\xi+\xi_1$), and ($\xi+\xi_2$).

Figure 22A:
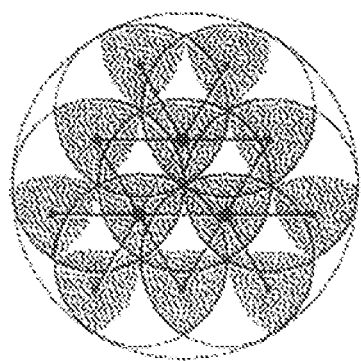
FIGS. 22A and 22B are explanatory drawings of Formula 1.63 in Section 1.9.

FIGS. 22A and B) are explanatory drawings of the 12 restoration points. Note that $|\xi_1|=|\xi_2|$ and $\xi_1\cdot\xi_2=|\xi_1||\xi_2|/2$.

The three large black spots in FIG. 22A represent the three observation points positioned at the peaks of the triangle formed from the three wave vectors $\xi_1$, $\xi_2$ and $\xi_3$ in the spectrum of each of the modulated images; and the three large black spots and the nine small black spots represent the restoration points (total of 12 restoration points) restored from these three observation points.

As described above, in this section, because the number of modulated images is set to four, a total of 12 observation values are acquired from three observation points. Restoration values of the 12 restoration points can be individually found by simultaneously solving the 12 formulas related to these 12 observation values.

In this section, by repeating the computation of the 12 restoration values while moving the three observation points, the restoration value of the entire darkened region in FIG. 22A can be found.

Figure 22B:
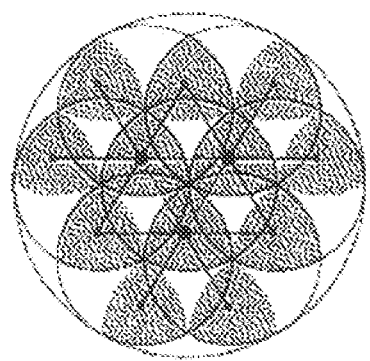

FIG. 22B is an explanatory drawing of a case where the direction of the triangle is inverted and restoration is performed as described above. It is possible to perform the restoration illustrated in FIG. 22A and the restoration illustrated in FIG. 22B in parallel. In this section, both restorations are performed and the same region as the darkened region illustrated in FIG. 20 is restored.

Here, the phases (formed from three components) of the three-direction interference fringes applied to each of the four modulated images $I^{(1)}$, $I^{(2)}$, $I^{(3)}$, and $I^{(4)}$ are, for example:

$$(\varphi_1^{(1)},\varphi_2^{(1)},\varphi_3^{(1)})=(0,0,0) \tag{1.65}$$

$$(\varphi_1^{(2)},\varphi_2^{(2)},\varphi_3^{(2)})=(\pi,0,\pi) \tag{1.66}$$

$$(\varphi_1^{(3)},\varphi_2^{(3)},\varphi_3^{(3)})=(0,\pi,-\pi) \tag{1.67}$$

$$(\varphi_1^{(4)},\varphi_2^{(4)},\varphi_3^{(4)})=(\pi,\pi,0) \tag{1.68}$$

That is, the interference fringe intensity distribution in each of the four modulated images $I^{(0)}$, $I^{(2)}$, $I^{(3)}$, and $I^{(4)}$ is as follows:

$$K_1(x) = 1 + 2a\left(\cos\left(\frac{2\pi}{\lambda}\xi_1 \cdot x\right) + \cos\left(\frac{2\pi}{\lambda}\xi_2 \cdot x\right) + \cos\left(\frac{2\pi}{\lambda}\xi_3 \cdot x\right)\right) \tag{1.69}$$

$$K_2(x) = 1 + 2a\left(-\cos\left(\frac{2\pi}{\lambda}\xi_1 \cdot x\right) + \cos\left(\frac{2\pi}{\lambda}\xi_2 \cdot x\right) - \cos\left(\frac{2\pi}{\lambda}\xi_3 \cdot x\right)\right) \tag{1.70}$$

$$K_3(x) = 1 + 2a\left(\cos\left(\frac{2\pi}{\lambda}\xi_1 \cdot x\right) - \cos\left(\frac{2\pi}{\lambda}\xi_2 \cdot x\right) - \cos\left(\frac{2\pi}{\lambda}\xi_3 \cdot x\right)\right) \tag{1.71}$$

$$K_4(x) = 1 + 2a\left(-\cos\left(\frac{2\pi}{\lambda}\xi_1 \cdot x\right) - \cos\left(\frac{2\pi}{\lambda}\xi_2 \cdot x\right) + \cos\left(\frac{2\pi}{\lambda}\xi_3 \cdot x\right)\right) \tag{1.72}$$

Moreover, the sum of the interference fringe intensity distribution in each of the four modulated images is as follows:

$$\sum_{i=1}^{4} K_i(x) = 1 \tag{1.73}$$

That is, as long as the four modulated images are acquired under the combination of the interference intensity distributions and phases described above, each part of the sample will be illuminated with an equivalent quantity of light. The four modulated images have a relationship in which the pattern of the three-direction interference fringes is common and only the position of the pattern is shifted. Thus, the following relationships are established.

$$K_2(x)=K_1(x+\tfrac{1}{2}a_1) \tag{1.74}$$

$$K_3(x)=K_1(x+\tfrac{1}{2}a_2) \tag{1.75}$$

$$K_4(x)=K_1(x+\tfrac{1}{2}a_1+\tfrac{1}{2}a_2) \tag{1.76}$$

Note that $a_1$ and $a_2$ are reference vectors of the grating when the periodic structure of the interference fringes is treated as a crystalline grating, and can be solved for in the following formulas when the reciprocal-grating vector (wave vector) $k_1$ is expressed $k_1=(2\pi/\lambda)\xi_1$, $k_2=(2\pi/\lambda)\xi_2$, and $k_3=e_z$ (where $e_z$ is the unit vector in the z-direction).

$$a_1 = 2\pi \frac{k_2 \times k_3}{k_1 \cdot (k_2 \times k_3)} \tag{1.77}$$

$$a_2 = 2\pi \frac{k_3 \times k_1}{k_2 \cdot (k_3 \times k_1)} \tag{1.78}$$

Figure 23:
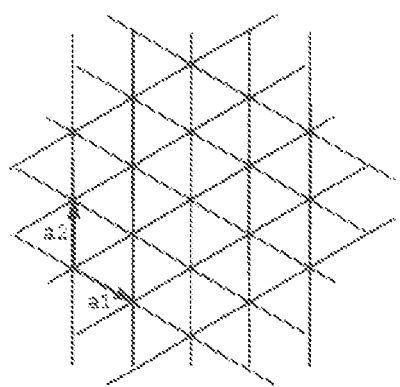
FIG. 23 is a drawing illustrating the relationship between the grating pattern of three-direction interference fringes and reference vectors $a_1$ and $a_2$ of the grating.

FIG. 23 is a drawing illustrating the relationship between the grating pattern of three-direction interference fringes and reference vectors $a_1$ and $a_2$ of the grating.

Figure 24:
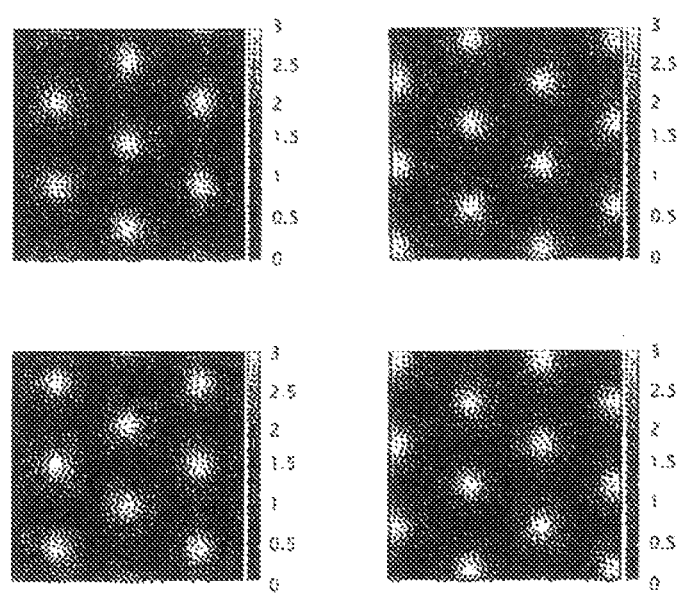
FIG. 24 is a drawing illustrating the interference fringe intensity distribution relationships between four modulated images.

FIG. 24 is a drawing illustrating the interference fringe intensity distribution relationships between four modulated images.

As illustrated in FIG. 24, the grating pattern moves in parallel between the four modulated images so that overlapping does not occur. Additionally, the unit of the amount of movement is half the reference vector of the grating.

<Section 1.92 (Method of Projecting the Three-Direction Interference Fringes)>

Next, the method of projecting the three-direction interference fringes will be described.

The diffraction grating 16 (FIG. 2A) described above can be used when causing the three-direction interference fringes to occur in the structured illumination microscope device described above, just as when causing other interference fringes (single-direction interference fringes) to occur.

Figures 25A, 25B:
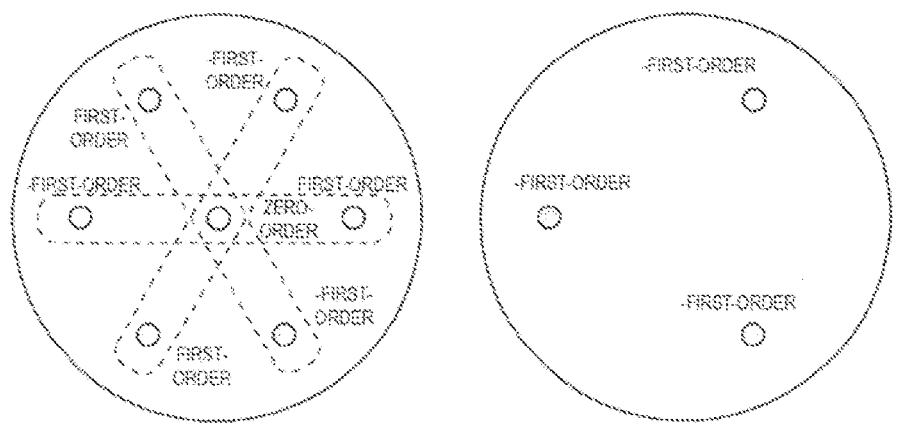
FIGS. 25A and 25B are drawings explaining a projection method of the three-direction interference fringes.

However, the aperture pattern of the beam selection member 20 is configured to cut the zero-order diffracted light beams of each group of the three groups of diffracted light beams generated by the diffraction grating 16, the second-order or higher-order diffracted light beams of each group, and the +first-order diffracted light beams of each group, and only transmit the −first-order diffracted light beams of each group. Thus, the focused light spot formed on the pupil plane will consist only of focused light spots formed by three −first-order diffracted light beams. FIG. 25A illustrates the arrangement of focused light spots in a case where the extra diffracted light beams are not cut by the beam selection member 20. FIG. 25B illustrates the arrangement of focused light spots in a case where the extra diffracted light beams are cut by the beam selection member 20. In the case of the latter, three focused light spots offset 120° from each other are formed. The diffracted light beams (here, the three −first-order diffracted light beams) emitted from these three focused light spots enter the illumination area of the sample from three directions and form a three-direction interference fringes on the sample. Note that here, the diffracted light beams contributing to the interference fringes are −first-order diffracted light beams, but it goes without saying that three +first-order diffracted light beams may be used.

However, when using +first-order diffracted light beams, super-resolution effects will decrease due to the occurrence of three-beam interference fringes instead of the superposition of three types of two-beam interference fringes. Additionally, use efficiency of the laser light will decrease due to the cutting of one of the ±first-order diffracted light beams.

Figure 26:
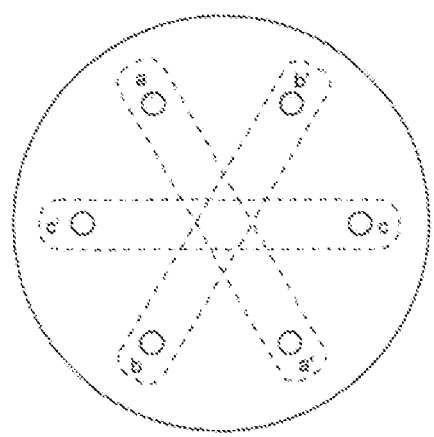
FIG. 26 is a drawing explaining another projection method of the three-direction interference fringes.

Accordingly, the following configuration may be used. Specifically, three individual laser light sources A, B, and C are prepared. Laser light emitted from the laser light source A, laser light emitted from the laser light source B, and laser light emitted from the laser light source C, are each split using a two-branch fiber to form six point light sources a, a', b, b', c, and c'. Note that the point light sources a and a' are coherent light sources generated from the laser light source A, the point light sources b and b' are coherent light sources generated from the laser light source B, and the point light sources c and c' are coherent light sources generated from the laser light source C. Moreover, the six light point sources a, a', b, b', c, and c' can be arranged on the pupil conjugate plane with positional relationships such as those shown in FIG. 26 by appropriately wiring the fiber. In other words, the arrangement direction of the point light sources a and a', the arrangement direction of the point light sources b and b', and the arrangement direction of the point light sources c and c' are set in differing directions, offset 120° from each other. The six laser light beams emitted from these six point light sources enter the illumination area of the sample from six directions and form three-direction interference fringes on the sample.

Here, the laser light La and La' emitted from the point light sources a and a', the laser light Lb and Lb' emitted from the point light sources b and b', and the laser light Lc and Lc' emitted from the point light sources c and c' do not interfere with each other. As such, the interference fringes formed on the sample is formed from the superposition of three types of two-beam interference fringes. Thus, the super-resolution effect will not decrease and the use efficiency of the laser light will be high.

Note that in cases such as that described above where a two-branch fiber is used instead of the diffraction grating 16 as the light branching unit, the phase difference between laser lights La and a', the phase difference between laser lights Lb and Lb', and the phase difference between laser lights Lc and Lc are each changed to change the phase (consisting of three components) of the three-direction interference fringes, instead of moving the diffraction grating 16.

<Section 2.1 (3D-SIM Premise)>

In this chapter, a 3D-SIM demodulation processing premise will be described.

Herein, "interference fringe intensity distribution in 3D-SIM" is defined as follows.

When the wavelength of three-beam interference is as $\lambda$, the interference fringe intensity distribution K(r) in 3D-SIM can be expressed as follows:

$$K(r) = \left| \sum_j a_j e^{ik_j \cdot r} \right|^2 \quad (2.1)$$

Where, vector $k_j$ is defined as follows where $k0=2\pi/\lambda$ and j=−1, 0, or +1.

$$k_0 = k_0 e_z, \quad (2.2)$$

$$k_+ = k_0(\sqrt{1-\xi_0^2}e_z + \xi_0) \quad (2.3)$$

$$k_- = k_0(\sqrt{1-\xi_0^2}e_z - \xi_0) \quad (2.4)$$

Here, $\xi_0 \cdot e_z = 0$.

When $a_0=1$, $a_+=a=|a|e^{i\varphi}$, and $a_-=a^*=|a|e^{-i\varphi}$ are assumed for the sake of simplification, the result is:

$$K(\tau) = |ae^{ik_+ \cdot r} + e^{ik_0 \cdot r} + a^*e^{ik_- \cdot r}|^2 \quad (2.5)$$

and the interference fringe intensity distribution K can be expressed as follows. The fringes are formed from the superposition of first periodic fringes (interference fringes formed by the left and right light among the three light beams, namely the center, left, and right light beams) having a sinusoidal intensity distribution, second periodic (two-times the first period) fringes having a sinusoidal intensity distribution (interference fringes formed by center light and the left and/or right light among the three light beams, namely the center, left, and right light beams).

$$K(x, z) = 1 + 2|a|^2 + a^* e^{i(k_- - k_0) \cdot r} + ae^{-i(k_- - k_0) \cdot r} + \\ ae^{i(k_+ - k_0) \cdot r} + a^* e^{-i(k_- - k_0) \cdot r} + a^{*2} e^{-i(k_+ - k_-) \cdot r} + a^2 e^{i(k_+ - k_-) \cdot r} \quad (2.6)$$

Here, when $\zeta_0 = \sqrt{[1-\xi_0^2]}-1$, K(x, z) can be expressed as:

$$K(x, z) = 1 + 2|a|^2 + a^*(e^{ik_0\zeta_0 z} + e^{-ik_0\zeta_0 z})e^{-ik_0\xi_0 \cdot x} + \quad (2.7)$$

$$a(e^{ik_0\zeta_0 z} + e^{-ik_0\zeta_0 z})e^{ik_0\xi_0 \cdot x} + a^{*2} e^{-2ik_0\xi_0 \cdot x} + a^2 e^{2ik_0\xi_0 \cdot x} \quad (2.8)$$

By isolating the component dependent on z and the component dependent on x, $$K(x, z) = \sum_{m=-2}^{2} K_m(z) J_m(x) \quad (2.9)$$

is possible. However, in this equation, $$K_0(z)=1 \quad (2.10)$$

$$K_{\pm 1}(z)=e^{ik_0\zeta_0 z}+e^{-ik_0\zeta z} \quad (2.11)$$

$$K_{\pm 2}(z)=1 \quad (2.12)$$

$$J_0=1+2|a|^2 \quad (2.13)$$

$$J_1=ae^{ik_0\xi_0 \cdot ae} \quad (2.14)$$

$$J_2=a^2 e^{2ik_0\xi_0 \cdot ae} \quad (2.15)$$

are defined. Furthermore, $J_{-1}=J_1^*$ and $J_{-2}=J_2^*$.

When $I_0(x)$ is the fluorescent substance density of the sample and the interference fringes having the interference fringe intensity distribution K described above are projected onto the sample, assuming the fluorescence light intensity distribution of the sample is expressed as $I_0(r)K(r)$, Born approximation is employed, that is, approximation is employed where the fluorescence light generated at each point in the sample does not excite the fluorescent substance at the other points.

Here, the modulated image I(x, z) acquired in 3D-SIM mode is expressed as follows:

$$I(x,z)=(I_o(x,z)K(x,z)) \otimes PSF(x,z) \quad (2.16)$$

That is, $$I(x, z) = \sum_m \int PSF(x-x', z-z') K_m(z) J_m(x, z) I_o(x, z) d^3x \quad (2.17)$$

Here, if the starting point of the z direction (O direction of the optical axis) of the interference fringes is set so that the z coordinate (z') of the observation point is always at the center, the modulated image I(x, z) is expressed as:

$$I(x, z) = \sum_m \int PSF(x-x', z-z')K_m(z-z')J_m(x, z')I_o(x, z')d^3x' \quad (2.18)$$

If the three-dimensional OTF is expressed as:

$$OTF_m(\xi,\zeta) = \mathcal{F}^{-1}[PSF(x,z)K_m(z)] \quad (2.19)$$

then, $$OTF_{\pm 2}(\xi,\zeta) = OTF_0(\xi,\zeta) \quad (2.20)$$

$$OTF_{\pm 1}(\xi,\zeta) = OTF_0(\xi,\zeta-\zeta_0) + OTF_0(\xi,\zeta+\zeta_0) \quad (2.21)$$

Moreover, the modulated image expressed in Fourier space (that is, the spatial frequency spectrum of the modulated image) is expressed as follows:

$$\tilde{I}(\xi, \zeta) = \sum_m OTF_m(\xi, \zeta)[\tilde{J}_m(\xi, \zeta) \otimes \tilde{I}_o(\xi, \zeta)] \quad (2.2)$$

When written in long-form:

$$\tilde{I}(\xi, \zeta) = OTF_0(\xi, \zeta)\tilde{I}_o(\xi, \zeta) + \quad (2.23)$$
$$b^*OTF_1(\xi, \zeta)\tilde{I}_o(\xi-\xi_0, \zeta) + bOTF_1(\xi, \zeta)\tilde{I}_o(\xi+\xi_0, \zeta) +$$
$$c^*OTF_0(\xi, \zeta)\tilde{I}_o(\xi-2\xi_0, \zeta) + cOTF_0(\xi, \zeta)\tilde{I}_o(\xi+2\xi_0, \zeta)$$

However, so that the coefficients of the first term equal one, $$b = \frac{|a|e^{i\phi}}{1+2|a|^2} \quad (2.24)$$

$$c = \frac{|a|^2 e^{2i\phi}}{1+2|a|^2} \quad (2.25)$$

Note that a, b, and c are values determined by the intensity balance of the three beams (the ±first-order diffracted light beams and the zero-order diffracted light beam) contributing to the 3D-SIM interference fringes.

Hereinafter, the spatial frequency spectrum in Fourier space is referred to simply as "spectrum". Additionally, φ, as it appears in the formulas, is referred to as "phase".

<Section 2.2 (Conventional 3D-SIM)>

In this section, demodulation processing in conventional 3D-SIM will be described for the purpose of comparison.

As described above, five components, namely the −first-order modulation component of the fluorescence light, the +first-order modulation component of the fluorescence light, the −second-order modulation component of the fluorescence light, the +second-order modulation component of the fluorescence light, and the zero-order modulation component of the fluorescence light, are superposed at the observation point $\xi$ of the spectrum of the modulated image acquired in the 3D-SIM mode. The ±first-order modulation component superposed at the observation point $\xi$ is a value (restoration value) that a restoration point $(\xi \pm \xi_0)$ in the spectrum of the demodulated image must have; the ±second-order modulation component superposed at the observation paint is a value (restoration value) that a restoration point $(\xi+2\xi_0)$ in the spectrum of the demodulated image must have; and the zero-order modulation component superposed at the observation point $\xi$ is a value (restoration value) that a restoration point $\xi$ in the spectrum of the demodulated image must have.

That is, the ±first-order modulation component superposed at the observation point $\xi$ is a component modulated by second periodic (two-times the first period) fringes having a sinusoidal intensity distribution (interference fringes formed by the center light and the left and/or right light among the three light beams, namely the center, left, and right light beams); and the ±second-order modulation component superposed at the observation point $\xi$ is a component modulated by first periodic fringes having a sinusoidal intensity distribution (Interference fringes formed by the left and right light among the three light beams, namely the center, left, and right light beams).

Figure 27A:
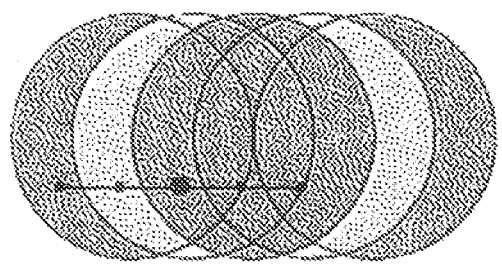
FIGS. 27A and 27B are drawings illustrating the frequency range of a demodulated image in conventional 3D-SIM.
Figure 27B:

This applies to each observation point in the spectrum of the modulated image. The large black spot in FIGS. 27A and 27B corresponds to an observation point, and the large black spot and the four small black spots on either side of the large black spot correspond to the five restoration points restored from the observation point.

In conventional 3D-SIM demodulation processing, in order to isolate each of the five modulation components superposed at each of the observation points in the spectrum of the modulated image, five modulated images having differing phases are acquired and a spectrum of each of the modulated images is generated. Conventionally, restoration values of the darkened regions in FIGS. 27A and 27B (normal resolution range and super-resolution range) are found by simultaneously solving five equations that these spectra satisfy.

<Section 2.4 (3D-SIM Nine-Image Two-Point Restoration)>

In this section, "nine-image two-point restoration" will be described as the 3D-SIM demodulation processing of the present embodiment. In this section, the control device 43 described above controls each constituent to acquire modulated images, and the image storage/processing device 44 executes the computations (the same holds true in other sections as well).

In this section, in the spectrum of one modulated image acquired through 3D-SIM, attention is called to the two observation points $\xi$ and $(\xi+\xi_0)$ separated from each other by the modulation frequency $\xi_0$ in the modulation direction, in which modulation components having a value in common are superposed.

Specifically, the −first-order modulation component of the fluorescence light superposed at the observation point $\xi$ and the zero-order modulation component of the fluorescence light superposed at the observation point $(\xi+\xi_0)$ both correspond to the restoration value of the restoration point $(\xi+\xi_0)$; the −second-order modulation component of the fluorescence light superposed at the observation point $\xi$ and the −first-order modulation component of the fluorescence light superposed at the observation point $(\xi+\xi_0)$ both correspond to the restoration value of the restoration point $(\xi+2\xi_0)$; the +first-order modulation component of the fluorescence light superposed at the observation point $(\xi+\xi_0)$ and the zero-order modulation component of the fluorescence light superposed at the observation point $\xi$ both correspond to the restoration value of the restoration point $\xi$; and the +second-order modulation component of the fluorescence light superposed at the observation point $(\xi+\xi_0)$ and the +first-order modulation component of the fluorescence light superposed at the observation point $\xi$ both correspond to the restoration value of the restoration point $(\xi-\xi_0)$. That is, common restoration values of the four restoration points $(\xi-\xi_0)$, $\xi$, $(\xi+\xi_0)$, and $(\xi+2\xi_0)$ are included in these two restoration points $\xi$ and $(\xi+\xi_0)$.

This relationship will be used in the nine-image two-point restoration discussed in this section. Hereinafter, a detailed description will be described.

The observation value of the observation point $\xi$ and the observation value of the observation point $(\xi+\xi 0)$ in the spectrum of the single modulated image are expressed in the following formulas.

$$\tilde{I}(\xi,\zeta) = OTF_0(\xi,\zeta)\tilde{I}_o(\xi,\zeta) + \\ b^*OTF_1(\xi,\zeta)\tilde{I}_o(\xi-\xi_0,\zeta) + bOTF_1(\xi,\zeta)\tilde{I}_o(\xi+\xi_0,\zeta) + \\ c^*OTF_0(\xi,\zeta)\tilde{I}_o(\xi-2\xi_0,\zeta) + cOTF_0(\xi,\zeta)\tilde{I}_o(\xi+2\xi_0,\zeta) \quad (2.31)$$

$$\tilde{I}(\xi+\xi_0,\zeta) = OTF_0(\xi+\xi_0,\zeta)\tilde{I}_o(\xi+\xi_0,\zeta) + \\ b^*OTF_1(\xi+\xi_0,\zeta)\tilde{I}_o(\xi,\zeta) + bOTF_1(\xi+\xi_0,\zeta)\tilde{I}_o(\xi+2\xi_0,\zeta) + \\ c^*OTF_0(\xi+\xi_0,\zeta)\tilde{I}_o(\xi-\xi_0,\zeta) + cOTF_0(\xi+\xi_0,\zeta)\tilde{I}_o(\xi+3\xi_0,\zeta) \quad (2.32)$$

Accordingly, in this section, a total of six formulas which include the six restoration values (unknowns) are acquired by acquiring three modulated images having differing phases $\varphi$, generating a spectrum of each of the three modulated images, referencing a total of six observation values related to the two observation points $\xi$ and $(\xi+\xi_0)$ from each of these three spectra, and applying these six observation values to the formulas.

Figure 28A:
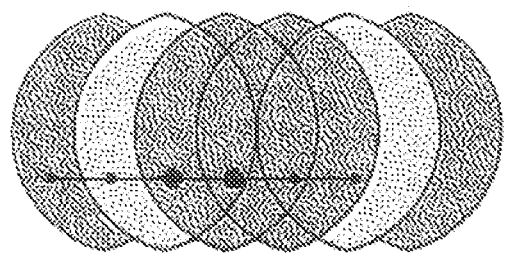
Figure 28B:
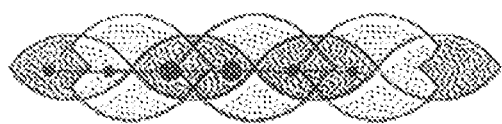

FIGS. 28A and 28B are drawings illustrating the frequency range of a demodulated image in the 3D-SIM of this section. FIG. 28A is an xy cross-section and FIG. 28B is a zx cross-section.

The large black spots in FIGS. 28A and 28B represent two observation points $\xi$ and $(\xi+\xi_0)$ separated from each other by $\xi_0$; and the two large black spots and the four small black spots in FIGS. 28A and 28B represent the restoration points (total of six restoration points) restored from the observation points $\xi$ and $(\xi+\xi_0)$.

The description below is a description of restoration based on one wave vector (single direction).

Thus, in this section, three modulated images having differing phases at each of three wave vectors having differing directions are acquired, a spectrum of each of the modulated images is generated, and the same restoration processing as that described above is performed on the spectra at each direction. Thereby, a demodulated image with a wide frequency range can be obtained.

Moreover, in this section, the phase difference $\Delta\varphi$ between the three modulated images acquired at the same wave vector is preferably set to $2\pi/3$.

<Section 2.5 (3D-SIM Seven-Image Three-Point Restoration)>

In this section, "seven-image three-point restoration" is described. The 3D-SIM of Section 1.7 using the spectrum of the unmodulated image is applied in this section.

First, in this section, the number of directions (number of wave vectors) is set to three.

Specifically, in this section, the three wave vectors $\xi_1$, $\xi_2$, and $\xi_3$ have a closed relationship ($\xi_3=\xi_1-\xi_2$), and instead of acquiring one unmodulated image, the number of phases of each of the three directions is reduced by one (i.e. set to two phases each).

Additionally, in this section, the phase difference $\Delta\varphi$ between the two modulated images acquired at the same wave vector is set to $\Delta\varphi\neq\pi$.

Here, where the three wave vectors are expressed as "k" (where k=1, 2, or 3), the two modulated images having differing phases acquired at the $k^{th}$ wave vector are expressed as follows:

$$I_{\varphi_k}^{(k)}, I_{\varphi_k+\Delta\varphi_k}^{(k)}$$

The unmodulated image is expressed as "$I^{(0)}$".

Thus, using Formula 2.23, the following formula is established.

$$\tilde{I}_{\varphi_k}^{(k)}(\xi,\zeta)=\tau_0\tilde{I}_o(\xi,\zeta)+\tau_0\tilde{I}_{1,\varphi_k}^{(k)}(\xi,\zeta)+\tau_0\tilde{I}_{2,\varphi_k}^{(k)}(\xi,\zeta) \quad (2.34)$$

However, the ±first-order modulation components and the ±second-order modulation components are consolidated and expressed as follows:

$$\tilde{I}_{1,\varphi_k}^{(k)}(\xi,\zeta)=|b_k|e^{-i\varphi k}\tilde{I}_o(\xi-\xi_k,\zeta)+|b_k|e^{i\varphi k}\tilde{I}_o(\xi+\xi_k,\zeta) \quad (2.35)$$

$$\tilde{I}_{2,\varphi_k}^{(k)}(\xi,\zeta)=|c_k|e^{-2i\varphi k}\tilde{I}_o(\xi-2\xi_k,\zeta)+|c_k|e^{2i\varphi k}\tilde{I}_o(\xi+2\xi_k,\zeta) \quad (2.36)$$

Furthermore, $\tau_0=OTF_0(\xi,\zeta)$ and $\tau_0'=OFT_1(\xi,\zeta)$. In this case, the phase difference $\Delta\varphi$ between the two modulated images acquired at the same wave vector is set to $\Delta\varphi\neq\pi$ and, therefore, the following formula is established, using Formula 2.35.

$$\tilde{I}_{1,\varphi_k+\pi}^{(k)}(\xi,\zeta)=-\tilde{I}_{1,\varphi_k}^{(k)}(\xi,\zeta) \quad (2.37)$$

$$\tilde{I}_{2,\varphi_k+\pi}^{(k)}(\xi,\zeta)=\tilde{I}_{2,\varphi_k}^{(k)}(\xi,\zeta) \quad (2.38)$$

As a result, the following formulas can be obtained from Formula 2.34.

$$\tilde{I}_{\varphi_k}^{(k)}(\xi,\zeta)=\tau_0\tilde{I}_o(\xi,\zeta)+\tau_0\tilde{I}_1^{(k)}(\xi,\zeta)+\tau_0\tilde{I}_2^{(k)}(\xi,\zeta) \quad (2.39)$$

$$\tilde{I}_{\varphi_k+\pi}^{(k)}(\xi,\zeta)=\tau_0\tilde{I}_o(\xi,\zeta)-\tau_0\tilde{I}_1^{(k)}(\xi,\zeta)+\tau_0\tilde{I}_2^{(k)}(\xi,\zeta) \quad (2.40)$$

Note that on the right side, the subscripts $\varphi k$ have been omitted for the sake of simplification.

Additionally, the zero-order modulation component (the normal resolution component) can be expressed as follows:

$$\tilde{I}^{(0)}(\xi,\zeta)=\tau_0\tilde{I}_o(\xi,\zeta) \quad (2.41)$$

The preceding formulas 2.39, 2.40, and 2.41 can be expressed as a matrix as follows:

$$\begin{bmatrix} \tilde{I}^{(0)}(\xi,\zeta) \\ \tilde{I}_{\phi_k}^{(k)}(\xi,\zeta) \\ \tilde{I}_{\phi_k+\pi}^{(k)}(\xi,\zeta) \end{bmatrix} = \begin{bmatrix} \tau_0 & 0 & 0 \\ \tau_0 & \tau_0' & \tau_0 \\ \tau_0 & -\tau_0' & \tau_0 \end{bmatrix} \begin{bmatrix} \tilde{I}_o(\xi,\zeta) \\ \tilde{I}_1^{(k)}(\xi,\zeta) \\ \tilde{I}_2^{(k)}(\xi,\zeta) \end{bmatrix} \quad (2.42)$$

Accordingly, in this section, first, by applying the seven observation values related to the observation point $\xi$ in the spectrum of each of the seven modulated images to Formula 2.42, the seven restoration values on the right side of Formula 2.42, that is, each of the following restoration values (the ±first-order modulation components, the ±second-order modulation components, and the zero-order modulation component) is found.

$$\tilde{I}_1^{(k)}, \tilde{I}_2^{(k)} (k=1,2,3), \tilde{I}_o$$

Calculations from this point forward are the same as the calculations performed in Section 1.7. Specifically, in the following spectrum:

$$\tilde{I}_1^{(k)}(k=1,2,3), \tilde{I}_0$$

if based on the 12 observation values related to any three observation points displaced from each other by the amount of the wave vector $\xi_k$ (where k=1, 2, or 3), the +first-order modulation component and the −first-order modulation component superposed at the three observation points can be isolated.

Additionally, in the following spectrum:

$$\tilde{I}_2^{(k)}(k=1,2,3), \tilde{J}_0$$

if based on the 12 observation values related to any three observation points displaced from each other by two-times the amount of the wave vector $\xi_k$ (where k=1, 2, or 3), the +second-order modulation component and the −second-order modulation component superposed at the three observation points can be isolated.

<Section 2.6 (3D-SIM Twelve-Image Three-Point Restoration)>

In this section, for the purpose of maintaining computation accuracy over the reduction in the number of images (the number of spectra), a total of 12 modulated images are acquired (a total of 12 spectra are generated) by setting the number of directions (the number of wave vectors) to three, and setting the number of phases of each direction to four.

Additionally, in this section, the phase difference $\Delta\varphi$ between the four modulated images acquired at the same wave vector is set to $\Delta\varphi=\pi/2$.

Here, the direction number is expressed as "k" (where k=1, 2, or 3) and the phase number is expressed as "l" (where l=0, 1, 2, or 3).

First the ±first-order modulation component is expressed from Formula 2.35:

$$\tilde{I}_{1,\varphi_k}^{(k)}(\xi,\zeta) = |b_k|e^{-i\varphi_k}\tilde{I}_o(\xi-\xi_k,\zeta) + |b_k|e^{i\varphi_k}\tilde{I}_o(\xi+\xi_k,\zeta) \quad (2.47)$$

$$\tilde{I}_{1,\varphi_k+\pi/2}^{(k)}(\xi,\zeta) = -i|b_k|e^{-i\varphi_k}\tilde{I}_o(\xi-\xi_k,\zeta) + i|b_k|e^{i\varphi_k}\tilde{I}_o(\xi+\xi_k,\zeta) \quad (2.48)$$

$$\tilde{I}_{1,\varphi_k+\pi}^{(k)}(\xi,\zeta) = -|b_k|e^{-i\varphi_k}\tilde{I}_o(\xi-\xi_k,\zeta) - |b_k|e^{i\varphi_k}\tilde{I}_o(\xi+\xi_k,\zeta) \quad (2.49)$$

$$\tilde{I}_{1,\varphi_k-\pi/2}^{(k)}(\xi,\zeta) = i|b_k|e^{-i\varphi_k}\tilde{I}_o(\xi-\xi_k,\zeta) - i|b_k|e^{i\varphi_k}\tilde{I}_o(\xi+\xi_k,\zeta) \quad (2.50)$$

and the ±second-order modulation component is expressed from Formula 2.36:

$$\tilde{I}_{2,\varphi_k}^{(k)}(\xi,\zeta) = |c_k|e^{-2i\varphi_k}\tilde{I}_o(\xi-2\xi_k,\zeta) + |c_k|e^{2i\varphi_k}\tilde{I}_o(\xi+2\xi_k,\zeta) \quad (2.51)$$

$$\tilde{I}_{2,\varphi_k+\pi/2}^{(k)}(\xi,\zeta) = -|c_k|e^{-2i\varphi_k}\tilde{I}_o(\xi-2\xi_k,\zeta) - |c_k|e^{2i\varphi_k}\tilde{I}_o(\xi+2\xi_k,\zeta) \quad (2.52)$$

$$\tilde{I}_{2,\varphi_k+\pi}^{(k)}(\xi,\zeta) = |c_k|e^{-2i\varphi_k}\tilde{I}_o(\xi-2\xi_k,\zeta) + |c_k|e^{2i\varphi_k}\tilde{I}_o(\xi+2\xi_k,\zeta) \quad (2.53)$$

$$\tilde{I}_{2,\varphi_k-\pi/2}^{(k)}(\xi,\zeta) = -|c_k|e^{-2i\varphi_k}\tilde{I}_o(\xi-2\xi_k,\zeta) - |c_k|e^{2i\varphi_k}\tilde{I}_o(\xi+2\xi_k,\zeta) \quad (2.54)$$

Accordingly, the following is established:

$$\tilde{I}_{2,\varphi_k}^{(k)}(\xi,\zeta) = \tilde{I}_{2,\varphi_k+\pi}^{(k)}(\xi,\zeta) = -\tilde{I}_{2,\varphi_k+\pi/2}^{(k)}(\xi,\zeta) = -\tilde{I}_{2,\varphi_k-\pi/2}^{(k)}(\xi,\zeta) \quad (2.55)$$

Thus, when expressed as a matrix, the demodulation processing of this section can be expressed:

$$\begin{bmatrix} \tilde{I}_{\phi_k}^{(k)}(\xi,\zeta) \\ \tilde{I}_{\phi_k+\frac{\pi}{2}}^{(k)}(\xi,\zeta) \\ \tilde{I}_{\phi_k+\pi}^{(k)}(\xi,\zeta) \\ \tilde{I}_{\phi_k-\frac{\pi}{2}}^{(k)}(\xi,\zeta) \end{bmatrix} = \begin{bmatrix} \tau_0 & \tau'_0 b_k^* & \tau'_0 b_k & \tau_0 \\ \tau_0 & -i\tau'_0 b_k^* & i\tau'_0 b_k & -\tau_0 \\ \tau_0 & -\tau'_0 b_k^* & -\tau'_0 b_k & \tau_0 \\ \tau_0 & i\tau'_0 b_k^* & -i\tau'_0 b_k & -\tau_0 \end{bmatrix} \begin{bmatrix} \tilde{I}_o(\xi,\zeta) \\ \tilde{I}_o(\xi-\xi_k,\zeta) \\ \tilde{I}_o(\xi+\xi_k,\zeta) \\ \tilde{I}_2^{(k)}(\xi,\zeta) \end{bmatrix} \quad (2.56)$$

Accordingly, in this section, the zero-order modulation component and the ±first-order modulation components can be isolated by applying the observation values of the spectra of the twelve modulated images (12 spectra) to this formula.

Moreover, the remaining ±second-order modulation components can be isolated by using the procedure detailed in Section 1.7.

Thus, in this section, high sectioning effects can be expected due to the fact that the ±first-order modulation components can be isolated without going through the procedure described in Section 2.5.

<Section 2.7 (3D-SIM Eight-Image Three-Point Restoration)>

Section 1.6 may be applied to 3D-SIM as follows.

In this section, the number of directions (number of wave vectors) is set to three.

Additionally, a closed relationship ($\xi_3=\xi_1-\xi_2$) is set for the three wave vectors $\xi_1$, $\xi_2$, and $\xi_3$.

Moreover, the number of phases for one direction among the three directions (wave vector $\xi_1$) is set to four, but the number of phases of the other two directions is limited to two.

That is, in this section, the number of unmodulated images in each of two of the directions is reduced by one instead of setting the relationship of the three wave vectors $\xi_1$, $\xi_2$, and $\xi_3$ to the closed relationship ($\xi_3=\xi_1-\xi_2$). Thus, the total number of modulated images (total number of spectra) will be eight.

However, in this section, the phase difference between the modulated images of the first direction (where k=1) is set to $\Delta\varphi=\pi/2$, the phase difference between the modulated images of the second direction (where k=2) is set to $\Delta\varphi=\pi$, and the phase difference between the modulated images of the third direction (where k=3) is set to $\Delta\varphi=\pi$.

It is possible to isolate each of the modulation components using the spectra of the eight modulated images acquired in this way. Specifically, the zero-order modulation component can be found from the spectra of the four modulated images related to the first direction (where k=1) in a first step and, thereafter, the ±first-order modulation components and the ±second-order modulation components can be isolated in a second step.

Note that in the preceding explanation, the number of wave vectors is set to three and the relationship between the three wave vectors $\xi_1$, $\xi_2$, and $\xi$ is set to be closed ($\xi_3=\xi_1-\xi_2$), but the number of wave vectors is not limited and may also be set to three or greater. For example, the number of wave vectors may be set to five and the relationship between these five wave vectors may be a closed relationship.

Embodiment of Continuously Observing Sample 2

An embodiment of continuously observing sample 2 will be described below. The operations of the control device 43 and the image storage/processing device 44 for continuously observing the sample 2, in a structured illumination microscope device for which 2D-SIM Sections 1.6 and 1.7 or 3D-SIM Sections 2.6 and 2.7 have been applied, are described.

Note that the while the number and types of images required for the aforementioned isolation (i.e. generation of the super-resolution image) may differ between 2D-SIM Sections 1.6 and 1.7 and 3D-SIM Sections 2.6 and 2.7, the basic operations are the same.

First, in order to continuously observe the sample 2, the control device 43 of the present embodiment repeats a series of processing in which N images, including M types of images (M≤N) required for the generation of a super-resolution image, are consecutively acquired. Hereinafter, this series of processing is referred to as a "round". In other words, N images are acquired in a first round, N images are acquired in a further second round, and N images are acquired in yet a further $n^{th}$ round.

Additionally, in order to continuously observe the sample 2, the image storage/processing device 44 of the present embodiment repeats the generation of a super-resolution image and the display of the super-resolution image. The generation of a super-resolution image and the display of the super-resolution image are performed as follows. Specifically, the image storage/processing device 44 carries out processing for generating one super-resolution image by selecting M types of images required for isolation (demodulation) from an image set of consecutive P images (image set consisting of P consecutive images) updated upon acquisition of L images (L≤M) on each of the image sets (M≤P≤N). Additionally, the image storage/processing device 44 displays the generated super-resolution images on the image display device 45 in the order generated. Thus, the super-resolution image on the image display device 45 is sequentially updated and continuous observation of the sample 2 is possible.

Hereinafter, the image acquisition, super-resolution image generation, and the super-resolution image displaying are carried out in parallel for the purpose of observing the sample 2 in real time. That is, the image storage/processing device 44 performs the generation of a super-resolution image upon acquisition of L images (L≤M) and the displaying of the super-resolution image upon generation of the super-resolution image.

Here, an image (a modulated image) wherein the interference fringes are shown is always included in the M types of images required to update the super-resolution image. At the time of acquiring this modulated image, the illumination intensity of the sample 2 becomes spatially nonuniform and, as a result, fading inconsistencies may occur on the sample 2.

Accordingly, the control device 43 of the present embodiment is configured such that the following conditions are satisfied for an arrangement of the N images in one round ("arrangement" means "arranging the images in a decided order" or "the order itself").

Uniformity condition: The intensity distribution of the interference fringes is spatially substantially uniform (substantially identical) when accumulated between N images (between images in the actual field of view). However, conditions at the time of image acquisition (determined by a combination of laser power, laser irradiation time, and charge storage time) are set to be common between the N images ("substantially uniform" indicates a state where the spatial variation of the intensity cumulative value in the formation region of the interference fringes is within 1% of the spatial average value of the intensity cumulative value).

Refresh condition; The image set consisting of the updated P images referenced at the time of refreshing of the super-resolution image (hereinafter, referred to simply as "the time of refreshing") always includes the M types of images required for refreshing the super-resolution image.

According to the present embodiment, within a round, the super-resolution image is refreshed upon acquisition of L images, and fading inconsistency on the sample 2 in the period from the beginning to the end of a round is eliminated. Therefore, there will be no worsening of the fading, even when the round is repeated multiple times.

Note that in the present embodiment, the number of images P constituting the image set (the image set constituted by P potential images for the purpose of selecting the M types of images required for refreshing; hereinafter referred to as "the referenced image set", or simply "the image set") referenced at the time of refreshing may be equal to the number of types of images M required for refreshing. That is, the refreshing of the super-resolution image may be performed by the constantly updated set of M images.

Additionally, in the present embodiment, the number of acquired images L corresponding to the refresh frequency of the super-resolution image may be one or two. That is, the refresh frequency of the super-resolution image may be "every one image" or "every two images". For example, when L=1, the image set prior to refreshing is constituted by a $1^{st}$ image to a $P^{th}$ image, and the image set at the time of refreshing is constituted by a $2^{nd}$ image to a $P+1^{th}$ image.

Alternatively, in the present embodiment, the number of acquired images L corresponding to the refresh frequency of the super-resolution image may be equal to the number of types of images M required for refreshing. That is, the refresh frequency of the super-resolution image may be "every M".

Additionally, in the present embodiment, the arrangement of the N images in one round may further fulfill the following conditions.

Direction condition: Direction switching of wave vectors within a round is limited to switching between directions that are adjacent to each other among the three directions of the wave vectors.

The significance of the direction condition is as follows. In cases where the relationships between the directions of the three wave vectors is, for example, as with the first direction V1, the second direction V2, and the third direction V3 illustrated in FIGS. 2A and 2B, the rotation position of a member (here, the beam selection member 20) used to switch the direction of the wave vector) may be switched among −60°, 0°, and +60°, with the direction V1 being the reference position (0°). However, while the beam selection member 20 must be rotated 60° in order to switch the rotation position of the beam selection member 20 between −60° and 0° and the beam selection member 20 must be rotated 60° in order to switch the rotation position of the beam selection member 20 between 0° and +60°, the beam selection member 20 must be rotated 120° in order to switch the rotation position of the beam selection member 20 between −60° and +60°. As such, the direction condition is useful for minimizing the rotation amount of the beam selection member 20.

Additionally, in the present embodiment, the arrangement of the N images in one round may further fulfill the following conditions.

Continuity condition: Among the M types of images required for refreshing, modulated images having a common wave vector are continuous within the image set referenced at the time of refreshing.

The significance of the continuity condition is as follows. Assuming that the acquisition timing of modulated images having a common wave vector is not continuous, and that the sample 2 changes prior to the completion of the acquisition of the modulated image, isolation accuracy would decrease and the image quality of the super-resolution image would decrease. Thus, the continuity condition is useful when changes over time of the sample 2 are considered.

Additionally, in the present embodiment, the arrangement of the N images in one round may further fulfill the following conditions.

Isotropy condition: Among the three wave vectors, the number of modulated images acquired at any one of the wave vectors, is equal to the number of modulated images acquired at any other of the wave vectors and the number of modulated images acquired at the remaining wave vector.

If this isotropy condition is fulfilled, there is a benefit in that the fading state of the sample 2 will be isotropic (the fading state between the three directions will be equal).

Example 1 of Continuously Observing Sample 2

Example 1 of the embodiment of continuously observing sample 2 will be described below.

In the present example, Section 1.7 of 2D-SIM mode is applied.

Therefore, the images required for refreshing the super-resolution image consist of one modulated image acquired at each of the three wave vectors having a mutually closed relationship, and one unmodulated image. Accordingly, the number of types of images M required for refreshing the super-resolution image is M=4.

Additionally, the refresh frequency of the super-resolution image is set to "every one image". That is, the number of acquired images L corresponding to the refresh frequency of the super-resolution image is set to L=1.

Additionally, the number of images P constituting the image set referenced at the time of refreshing is equal to the number of types of images M required for refreshing. In other words, the number of images P constituting the image set is P=M=4.

Moreover, in the present example, the arrangement of the N images in one round is set as shown in Table 1 so as to fulfill the uniformity condition and the refresh condition described above. With the arrangement of Table 1, the number of acquired images N in one round is N=8.

TABLE 1

| | |
|---|---|
| Image 1 | Unmodulated image |
| Image 2 | Direction 1, phase θ1 modulated image |
| Image 3 | Direction 2, phase θ2 modulated image |
| Image 4 | Direction 3, phase θ3 modulated image |
| Image 5 | Unmodulated image |
| Image 6 | Direction 1, phase θ1 + π modulated image |
| Image 7 | Direction 2, phase θ2 + π modulated image |
| Image 8 | Direction 3, phase θ3 + π modulated image |

Note that the directions in Table 1 represent the direction of the wave vector, the phases represent the phase of the wave vector, and the image numbers represent the acquisition order of the images. Additionally, direction 1, direction 2, direction 3, and phases θ1, θ2, and θ3 in Table 1 are each optional. The relationship between direction 1, direction 2, and direction 3 may, for example, be the relationship between the first direction V1, the second direction V2, and the third direction V3, as illustrated in FIGS. 2A and 2B.

Moreover, in the present example, the images used in refreshing the super-resolution image are the combinations shown in Table 2.

TABLE 2

| | |
|---|---|
| Super-resolution image 1 | Image 1, Image 2, Image 3, Image 4 |
| Super-resolution image 2 | Image 2, Image 3, Image 4, Image 5 |
| Super-resolution image 3 | Image 3, Image 4, Image 5, Image 6 |
| Super-resolution image 4 | Image 4, Image 5, Image 6, Image 7 |
| Super-resolution image 5 | Image 5, Image 6, Image 7, Image 8 |

Note that the super-resolution image numbers in Table 2 represent the generation order of the super-resolution images.

Example 2 of Continuously Observing Sample 2

Example 2 of the embodiment of continuously observing sample 2 will be described below.

The present example is a variation of example 1, and therefore only the differences between the present example and example 1 will be described here.

In the present example, the direction condition is added to those used in example 1 and the refresh condition is relaxed.

In order to relax the refresh condition, in the present example, the refresh frequency of the super-resolution image is reduced to "every four" (L=4).

Thus, in the present example, the arrangement of the N images in one round is set as shown in Table 3 so as to fulfill the uniformity condition, the refresh condition (where L=4), and the direction condition. With the arrangement of Table 3, the number of acquired images N in one round is N=8.

TABLE 3

| | |
|---|---|
| Image 1 | Unmodulated image |
| Image 2 | Direction 1, phase θ1 modulated image |
| Image 3 | Direction 2, phase θ2 modulated image |
| Image 4 | Direction 3, phase θ3 modulated image |
| Image 5 | Direction 3, phase θ3 + π modulated image |
| Image 6 | Direction 2, phase θ2 + π modulated image |
| Image 7 | Direction 1, phase θ1 + π modulated image |
| Image 8 | Unmodulated image |

Note that the directions in Table 3 represent the direction of the wave vector, the phases represent the phase of the wave vector, and the image numbers represent the acquisition order of the images. Additionally, while the phases θ1, θ2, and θ3 in Table 1 are each optional, it is assumed that direction 1 and direction 2 are directions that are adjacent to each other, direction 2 and direction 3 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 4.

TABLE 4

| | |
|---|---|
| Super-resolution image 1 | Image 1, Image 2, Image 3, Image 4 |
| Super-resolution image 2 | Image 5, Image 6, Image 7, Image 8 |
| Super-resolution image 3 | Image 9, image 10, Image 11, Image 12 |

As described, in the present example, while the refresh frequency of the super-resolution image is less than the refresh frequency in example 1, there is a benefit in that the direction switching of the interference fringes can be optimized.

Example 3 of Continuously Observing Sample 2

Example 3 of the embodiment of continuously observing sample 2 will be described below.

In this example, Section 1.6 of 2D-SIM mode is applied.

Therefore, the images required for refreshing the super-resolution image consist of, among the three wave vectors having a mutually closed relationship, two modulated images acquired at each of two wave vectors, and two unmodulated images having differing phases acquired at the remaining wave vector. Accordingly, the number of types of images M required for refreshing the super-resolution image is M=4.

Additionally, the refresh frequency of the super-resolution image is set to "every one image". That is, L is set so that L=1.

Additionally, the number of images P constituting the image set referenced at the time of refreshing is equal to the number of types of images M required for refreshing. In other words, the number of images P constituting the image set is P=M=4.

Moreover, in the present example, the arrangement of the N images in one round is set as shown in Table 5 so as to fulfill the uniformity condition, the refresh condition, and the continuity condition described above. With the arrangement of Table 5, the number of acquired images N in one round is N=18.

TABLE 5

| Image 1 | Direction 1, phase $\theta 1$ modulated image |
|---|---|
| Image 2 | Direction 2, phase $\phi 2$ modulated image |
| Image 3 | Direction 3, phase $\theta 3$ modulated image |
| Image 4 | Direction 3, phase $\theta 3 + \pi$ modulated image |
| Image 5 | Direction 1, phase $\phi 1 + \pi$ modulated image |
| Image 6 | Direction 2, phase $\theta 2 + \pi$ modulated image |
| Image 7 | Direction 2, phase $\theta 2$ modulated image |
| Image 8 | Direction 3, phase $\phi 3$ modulated image |
| Image 9 | Direction 1, phase $\theta 1'$ modulated image |
| Image 10 | Direction 1, phase $\theta 1' + \pi$ modulated image |
| Image 11 | Direction 2, phase $\phi 2 + \pi$ modulated image |
| Image 12 | Direction 3, phase $\theta 3' + \pi$ modulated image |
| Image 13 | Direction 3, phase $\theta 3'$ modulated image |
| Image 14 | Direction 1, phase $\phi 1$ modulated image |
| Image 15 | Direction 2, phase $\theta 2'$ modulated image |
| Image 16 | Direction 2, phase $\theta 2' + \pi$ modulated image |
| Image 17 | Direction 3, phase $\phi 3 + \pi$ modulated image |
| Image 18 | Direction 1, phase $\theta 1 + \pi$ modulated image |

Note that the directions in Table 5 represent the direction of the wave vector, the phases represent the phase of the wave vector, and the image numbers represent the acquisition order of the images. Additionally, direction 1, direction 2, and direction 3; phases $\theta 1$, $\theta 1'$, $\theta 2$, $\theta 2'$, $\theta 3$, and $\theta 3'$; and $\phi 1$, $\phi 2$, and $\phi 3$ in Table 5 are each optional. The relationship between direction 1, direction 2, and direction 3 may, for example, be the relationship between the first direction V1, the second direction V2, and the third direction V3 (see FIGS. 2A and 2B).

Moreover, in the present example, the images used in refreshing the super-resolution image are the combinations shown in Table 6.

TABLE 6

| Super-resolution image 1 | Image 1, Image 2, Image 3, Image 4 |
|---|---|
| Super-resolution image 2 | Image 2, Image 3, Image 4, Image 5 |
| Super-resolution image 3 | Image 3, Image 4, Image 5, Image 6 |
| Super-resolution image 4 | Image 4, Image 5, Image 6, Image 7 |
| Super-resolution image 5 | Image 5, Image 6, Image 7, Image 8 |
| Super-resolution image 6 | Image 6, Image 7, Image 8, Image 9 |
| Super-resolution image 7 | Image 7, Image 8, Image 9, Image 10 |
| Super-resolution image 8 | Image 8, Image 9, Image 10, Image 11 |
| Super-resolution image 9 | Image 9, Image 10, Image 11, Image 12 |
| Super-resolution image 10 | Image 10, Image 11, Image 12, Image 13 |
| Super-resolution image 11 | Image 11, Image 12, Image 13, Image 14 |
| Super-resolution image 12 | Image 12, Image 13, Image 14, Image 15 |
| Super-resolution image 13 | Image 13, Image 14, Image 15, Image 16 |
| Super-resolution image 14 | Image 14, Image 15, Image 16, Image 17 |
| Super-resolution image 15 | Image 15, Image 16, Image 17, Image 18 |

Note that the super-resolution image numbers in Table 6 represent the generation order of the super-resolution images.

Additionally, in the present example, because the isotropy condition described above is fulfilled, there is a benefit in that the fading state of the sample 2 will be isotropic.

In the present example, the following settings may particularly be made: $\theta 1 = \phi 1$, $\theta 2 = \phi 2$, $\theta 3 = \phi 3$. In this case, the arrangement of the N images will be as shown in Table 7 and the images used in refreshing the super-resolution image will be the combinations shown in Table 8.

TABLE 7

| Image 1 | Direction 1, phase $\theta 1$ modulated image |
|---|---|
| Image 2 | Direction 2, phase $\theta 2$ modulated image |
| Image 3 | Direction 3, phase $\theta 3$ modulated image |
| Image 4 | Direction 3, phase $\theta 3 + \pi$ modulated image |
| Image 5 | Direction 1, phase $\theta 1 + \pi$ modulated image |
| Image 6 | Direction 2, phase $\theta 2 + \pi$ modulated image |
| Image 7 | Direction 2, phase $\theta 2$ modulated image |
| Image 8 | Direction 3, phase $\theta 3$ modulated image |
| Image 9 | Direction 1, phase $\theta 1$ modulated image |
| Image 10 | Direction 1, phase $\theta 1 + \pi$ modulated image |
| Image 11 | Direction 2, phase $\theta 2 + \pi$ modulated image |
| Image 12 | Direction 3, phase $\theta 3 + \pi$ modulated image |
| Image 13 | Direction 3, phase $\theta 3$ modulated image |
| Image 14 | Direction 1, phase $\theta 1$ modulated image |
| Image 15 | Direction 2, phase $\theta 2$ modulated image |
| Image 16 | Direction 2, phase $\theta 2 + \pi$ modulated image |
| Image 17 | Direction 3, phase $\theta 3 + \pi$ modulated image |
| Image 18 | Direction 1, phase $\theta 1 + \pi$ modulated image |

TABLE 8

| Super-resolution image 1 | Image 1, Image 2, Image 3, Image 4 |
|---|---|
| Super-resolution image 2 | Image 2, Image 3, Image 4, Image 5 |
| Super-resolution image 3 | Image 3, Image 4, Image 5, image 6 |
| Super-resolution image 4 | Image 4, Image 5, Image 6, Image 7 |
| Super-resolution image 5 | Image 5, Image 6, Image 7, Image 8 |
| Super-resolution image 6 | Image 6, Image 7, Image 8, Image 9 |
| Super-resolution image 7 | Image 7, Image 8, Image 9, Image 10 |
| Super-resolution image 8 | Image 8, Image 9, Image 10, Image 11 |
| Super-resolution image 9 | Image 9, Image 10, Image 11, Image 12 |
| Super-resolution image 10 | Image 10, Image 11, Image 12, Image 13 |
| Super-resolution image 11 | Image 11, Image 12, Image 13, Image 14 |
| Super-resolution image 12 | Image 12, Image 13, Image 14, Image 15 |
| Super-resolution image 13 | Image 13, Image 14, Image 15, Image 16 |
| Super-resolution image 14 | Image 14, Image 15, Image 16, Image 17 |
| Super-resolution image 15 | Image 15, Image 16, Image 17, Image 18 |

Using these settings, a further benefit can be obtained in that fading inconsistencies on the sample 2 can be eliminated on a frequent basis. Moreover, while the elimination frequency of fading inconsistencies for the arrangement of Table 5 is "every 18 images", the elimination frequency of fading inconsistencies for the arrangement of Table 7 is "every six images".

Example 4 of Continuously Observing Sample 2

Example 4 of the embodiment of continuously observing sample 2 will be described below.

The present example is a variation of example 3, and therefore only the differences between the present example and example 3 will be described here.

In the present example, the direction condition is added to those used in example 3 and the refresh condition is relaxed.

In order to relax the refresh condition, in the present example, the refresh frequency of the super-resolution image is reduced to "every four images" (L=4).

Thus, in the present example, the arrangement of the N images in one round is set as shown in Table 9 so as to fulfill the uniformity condition, the refresh condition (where L=4), the continuity condition, and the direction condition. With the arrangement of Table 9, the number of acquired images N in one round is N=12.

TABLE 9

| Image 1 | Direction 1, phase θ1 modulated image |
|---|---|
| Image 2 | Direction 2, phase θ2 modulated image |
| Image 3 | Direction 3, phase θ3 modulated image |
| Image 4 | Direction 3, phase θ3 + π modulated image |
| Image 5 | Direction 3, phase θ3 + π modulated image |
| Image 6 | Direction 2, phase θ2 + π modulated image |
| Image 7 | Direction 1, phase θ1 + π modulated image |
| Image 8 | Direction 1, phase θ1 modulated image |
| Image 9 | Direction 1, phase θ1 + π modulated image |
| Image 10 | Direction 2, phase θ2 + π modulated image |
| Image 11 | Direction 2, phase θ2 modulated image |
| Image 12 | Direction 3, phase θ3 modulated image |

Note that the directions in Table 9 represent the direction of the wave vector, the phases represent the phase of the wave vector, and the image numbers represent the acquisition order of the images. Additionally, while the phases θ1, θ2, and θ3 in Table 1 are each optional, it is assumed that direction 1 and direction 2 are directions that are adjacent to each other, direction 2 and direction 9 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 10.

TABLE 10

| Super-resolution image 1 | Image 1, Image 2, Image 3, Image 4 |
|---|---|
| Super-resolution image 2 | Image 5, Image 6, Image 7, Image 8 |
| Super-resolution image 3 | Image 9, Image 10, Image 11, Image 12 |

As described, in the present example, while the refresh frequency of the super-resolution image is less than the refresh frequency in example 3, there is a benefit in that the direction switching of the interference fringes can be optimized.

Example 5 of Continuously Observing Sample 2

Example 5 of the embodiment of continuously observing sample 2 will be described below.

The present example is a variation of example 3, and therefore only the differences between the present example and example 3 will be described here.

In the present example, the direction condition is added to those used in example 3 and the continuity condition is removed.

Thus, in the present example, the arrangement of the N images in one round is set as shown in Table 11 so as to fulfill the uniformity condition, the refresh condition (where L=1), and the direction condition. With the arrangement of Table 11, the number of acquired images N in one round is N=8.

TABLE 11

| Image 1 | Direction 1, phase θ1 modulated image |
|---|---|
| Image 2 | Direction 2, phase θ2 modulated image |
| Image 3 | Direction 3, phase θ3 modulated image |
| Image 4 | Direction 2, phase θ2 + π modulated image |
| Image 5 | Direction 1, phase θ1 + π modulated image |
| Image 6 | Direction 2, phase θ2 modulated image |
| Image 7 | Direction 3, phase θ3 + π modulated image |
| Image 8 | Direction 2, phase θ2 + π modulated image |

Note that the directions in Table 11 represent the direction of the wave vector, the phases represent the phase of the wave vector, and the image numbers represent the acquisition order of the images. Additionally, while the phases θ1, θ2, and θ3 in Table 11 are each optional, it is assumed that direction 1 and direction 2 are directions that are adjacent to each other, direction 2 and direction 11 are directions that are adjacent to each other, but direction 1 and direction 3 are directions that are not adjacent to each other.

Moreover, in the present example, the images used in refreshing the super-resolution image are the combinations shown in Table 12.

TABLE 12

| Super-resolution image 1 | Image 1, Image 2, Image 3, Image 4 |
|---|---|
| Super-resolution image 2 | Image 2, Image 3, Image 4, Image 5 |
| Super-resolution image 3 | Image 3, Image 4, Image 5, Image 6 |
| Super-resolution image 4 | Image 4, Image 5, Image 6, Image 7 |
| Super-resolution image 5 | Image 5, Image 6, Image 7, Image 8 |

As described, in the present example, the acquisition timing of two modulated images having a common direction of the interference fringes is not continuous and, therefore, while the present example is not suitable for samples 2 where the change over time is great, there is a benefit in that the direction switching of the interference fringes can be optimized.

Example 6 of Continuously Observing Sample 2

Example 6 of the embodiment of continuously observing sample 2 will be described below.

The present example is a variation of example 3, and therefore only the differences between the present example and example 3 will be described here.

In the present example, the direction condition is added to those used in example 3 and the refresh condition is relaxed.

In order to relax the refresh condition, in the present example, the number of images P constituting the image set referenced at the time of refreshing is increased by one image (where P=5). In this case, the images used for refreshing are not the "four newest images", but instead, the "appropriate four images among the newest five images".

Thus, in the present example, the arrangement of the N images in one round is set as shown in Table 13 so as to fulfill the uniformity condition, the refresh condition (where P=5), the continuity condition, and the direction condition. With the arrangement of Table 13, the number of acquired images N in one round is N=6.

TABLE 13

| Image 1 | Direction 1, phase θ1 modulated image |
|---|---|
| Image 2 | Direction 2, phase θ2 modulated image |
| Image 3 | Direction 3, phase θ3 modulated image |
| Image 4 | Direction 3, phase θ3 + π modulated image |
| Image 5 | Direction 2, phase θ2 + π modulated image |
| Image 6 | Direction 1, phase θ1 + π modulated image |

Note that the directions in Table 13 represent the direction of the wave vector, the phases represent the phase of the wave vector, and the image numbers represent the acquisition order of the images. Additionally, while the phases $\theta1$, $\theta2$, and $\theta3$ in Table 13 are each optional, it is assumed that direction 1 and direction 2 are directions that are adjacent to each other, direction 2 and direction 3 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 14.

TABLE 14

| | |
|---|---|
| Super-resolution image 1 | Image 1, Image 2, Image 3, Image 4 |
| Super-resolution image 2 | Image 1, Image 3, Image 4, Image 5 |
| Super-resolution image 3 | Image 3, Image 4, Image 5, Image 6 |
| Super-resolution image 4 | Image 4, Image 5, Image 6, Image 1' |
| Super-resolution image 5 | Image 4, Image 6, Image 1', Image 2' |
| Super-resolution image 6 | Image 6, Image 1', Image 2', Image 3' |
| Super-resolution image 7 | Same as Super-resolution Image 1 |

Note that the image numbers 1, 2, 3 . . . in Table 14 are the image numbers in the first round, the image numbers 1', 2', 3' . . . are the image numbers in the second round (this applies to other tables).

As described, in the present example, while the images used in the refreshing of the super-resolution image are not always the newest four images, there is a benefit in that the direction switching of the interference fringes can be optimized.

Example 7 of Continuously Observing Sample 2

Example 7 of the embodiment of continuously observing sample 2 will be described below.

In the present example, another arrangement fulfilling the same conditions as in Example 4 (uniformity condition, refresh condition (where L=4), continuity condition, and direction condition) is described.

The arrangement of the present example is as shown in Table 15. With the arrangement of Table 15, the number of acquired images N in one round is N=24.

TABLE 15

| | |
|---|---|
| Image 1 | Direction 1, phase $\theta1$ modulated image |
| Image 2 | Direction 2, phase $\theta2$ + $\pi$ modulated image |
| Image 3 | Direction 2, phase $\theta2$ modulated image |
| Image 4 | Direction 3, phase $\theta3$ modulated image |
| Image 5 | Direction 3, phase $\theta3$ + $\pi$ modulated image |
| Image 6 | Direction 2, phase $\theta2$ + $\pi$ modulated image |
| Image 7 | Direction 1, phase $\theta1$ + $\pi$ modulated image |
| Image 8 | Direction 1, phase $\theta1$ modulated image |
| Image 9 | Direction 1, phase $\theta1$ + $\pi$ modulated image |
| Image 10 | Direction 1, phase $\theta1$ modulated image |
| Image 11 | Direction 2, phase $\theta2$ modulated image |
| Image 12 | Direction 3, phase $\theta3$ modulated image |
| Image 13 | Direction 3, phase $\theta3$ + $\pi$ modulated image |
| Image 14 | Direction 2, phase $\theta2$ modulated image |
| Image 15 | Direction 2, phase $\theta2$ + $\pi$ modulated image |
| Image 16 | Direction 1, phase $\theta1$ + $\pi$ modulated image |
| Image 17 | Direction 1, phase $\theta1$ modulated image |
| Image 18 | Direction 2, phase $\theta2$ modulated image |
| Image 19 | Direction 3, phase $\theta3$ modulated image |
| Image 20 | Direction 3, phase $\theta3$ + $\pi$ modulated image |
| Image 21 | Direction 3, phase $\theta3$ modulated image |
| Image 22 | Direction 3, phase $\theta3$ + $\pi$ modulated image |
| Image 23 | Direction 2, phase $\theta2$ + $\pi$ modulated image |
| Image 24 | Direction 1, phase $\theta1$ + $\pi$ modulated image |

Note that the directions in Table 15 represent the direction of the wave vector, the phases represent the phase of the wave vector, and the image numbers represent the acquisition order of the images. Additionally, while the phases $\theta1$, $\theta2$, and $\theta3$ in Table 15 are each optional, it is assumed that direction 1 and direction 2 are directions that are adjacent to each other, direction 2 and direction 3 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 16.

TABLE 16

| | |
|---|---|
| Super-resolution image 1 | Image 1, Image 2, Image 3, Image 4 |
| Super-resolution image 2 | Image 5, Image 6, Image 7, Image 8 |
| Super-resolution image 3 | Image 9, Image 10, Image 11, Image 12 |
| Super-resolution image 4 | Image 13, Image 14, Image 15, Image 16 |
| Super-resolution image 5 | Image 17, Image 18, Image 19, Image 20 |
| Super-resolution image 6 | Image 21, Image 22, Image 23, Image 24 |

As described, in the present example, even though the number of acquired images N in one round is greater than that in Example 4, the same benefits can be obtained.

Example 8 of Continuously Observing Sample 2

Example 8 of the embodiment of continuously observing sample 2 will be described below.

In the present example, Section 2.5 of 3D-SIM mode is applied.

Therefore, the images required for refreshing the super-resolution image consist of, among the three wave vectors having a mutually closed relationship, two modulated images having differing phases acquired at one wave vector, two modulated images having differing phases acquired at another wave vector, two modulated images having differing phases acquired at the remaining wave vector, and one unmodulated image. Accordingly, the number of types of images M required for refreshing the super-resolution image is M=7.

Additionally, the refresh frequency of the super-resolution image is set to "every two images" or "every one image". That is, L is set so that L=1 or L=2.

Additionally, the number of images P constituting the image set referenced at the time of refreshing is equal to the number of types of images M required for refreshing. In other words, the number of images P constituting the image set is P=M=7.

Moreover, in the present example, the arrangement of the N images in one round is set as shown in Table 17 so as to fulfill the uniformity condition, the refresh condition, and the continuity condition described above. With the arrangement of Table 17, the number of acquired images N in one round is N=14.

TABLE 17

| Image 1 | Unmodulated image |
|---|---|
| Image 2 | Direction 1, phase θ1 modulated image |
| Image 3 | Direction 1, phase θ1 + π modulated image |
| Image 4 | Direction 2, phase θ2 modulated image |
| Image 5 | Direction 2, phase θ2 + π modulated image |
| Image 6 | Direction 3, phase θ3 modulated image |
| Image 7 | Direction 3, phase θ3 + π modulated image |
| Image 8 | Unmodulated image |
| Image 9 | Direction 1, phase θ1 + π/2 modulated image |
| Image 10 | Direction 1, phase θ1 + 3π/2 modulated image |
| Image 11 | Direction 2, phase θ2 + π/2 modulated image |
| Image 12 | Direction 2, phase θ2 + 3π/2 modulated image |
| Image 13 | Direction 3, phase θ3 + π/2 modulated image |
| Image 14 | Direction 3, phase θ3 + 3π/2 modulated image |

Note that the directions in Table 17 represent the direction of the wave vector, the phases represent the phase of the wave vector, and the image numbers represent the acquisition order of the images. Additionally, direction 1, direction 2, direction 3, and phases θ1, θ2, and θ3 in Table 17 are each optional. The relationship between direction 1, direction 2, and direction 3 may, for example, be the relationship between the first direction V1, the second direction V2, and the third direction V3.

Moreover, in the present example, the images used in refreshing the super-resolution image are the combinations shown in Table 18.

TABLE 18

| Super-resolution image 1 | Images 1, 2, 3, 4, 5, 6, and 7 |
|---|---|
| Super-resolution image 2 | Images 2, 3, 4, 5, 6, 7, and 8 |
| Super-resolution image 3 | Images 4, 5, 6, 7, 8, 9, and 10 |
| Super-resolution image 4 | Images 6, 7, 8, 9, 10, 11, and 12 |
| Super-resolution image 5 | Images 8, 9, 10, 11, 12, 13, and 14 |
| Super-resolution image 6 | Images 9, 10, 11, 12, 13, 14, and 1' |
| Super-resolution image 7 | Images 11, 12, 13, 14, 1', 2', and 3' |
| Super-resolution image 8 | Images 13, 14, 1', 2', 3', 4', and 5' |
| Super-resolution image 9 | Images, 1', 2', 3', 4', 5', 6', and 7' |

Note that the super-resolution image numbers in Table 18 represent the generation order of the super-resolution images.

As described, in Example 8, fundamentally, the super-resolution image is refreshed upon acquisition of both of two modulated images having a common wave vector and differing phases (that is, the super-resolution image is refreshed fundamentally every two images). However, in Example 8, the super-resolution image is also refreshed upon acquisition of the unmodulated image (that is, the super-resolution image is refreshed upon acquisition of every one unmodulated image).

Example 9 of Continuously Observing Sample 2

Example 9 of the embodiment of continuously observing sample 2 will be described.

The present example is a variation of example 8, and therefore only the differences between the present example and example 8 will be described here.

In the present example, the direction condition is added to those used in example 8 and the refresh condition is relaxed.

In order to relax the refresh condition, in the present example, the refresh frequency of the super-resolution image is reduced to "every seven images" (L=7).

That is, in the present example, the arrangement of the N images in one round is set as shown in Table 19 so as to fulfill the uniformity condition, the refresh condition (where L=7), the continuity condition, and the direction condition.

With the arrangement of Table 19, the number of acquired images N in one round is N=14.

TABLE 19

| Image 1 | Unmodulated image |
|---|---|
| Image 2 | Direction 1, phase θ1 modulated image |
| Image 3 | Direction 1, phase θ1 + π modulated image |
| Image 4 | Direction 2, phase θ2 modulated image |
| Image 5 | Direction 2, phase θ2 + π modulated image |
| Image 6 | Direction 3, phase θ3 modulated image |
| Image 7 | Direction 3, phase θ3 + π modulated image |
| Image 8 | Direction 3, phase θ3 + π/2 modulated image |
| Image 9 | Direction 3, phase θ3 + 3π/2 modulated image |
| Image 10 | Direction 2, phase θ2 + π/2 modulated image |
| Image 11 | Direction 2, phase θ2 + 3π/2 modulated image |
| Image 12 | Direction 1, phase θ1 + π/2 modulated image |
| Image 13 | Direction 1, phase θ1 + 3π/2 modulated image |
| Image 14 | Unmodulated image |

Note that the directions in Table 19 represent the direction of the wave vector, the phases represent the phase of the wave vector, and the image numbers represent the acquisition order of the images. Additionally, while the phases θ1, θ2, and θ3 in Table 19 are each optional, it is assumed that direction 1 and direction 2 are directions that are adjacent to each other, direction 2 and direction 3 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 20.

TABLE 20

| Super-resolution image 1 | Images 1, 2, 3, 4, 5, 6, and 7 |
|---|---|
| Super-resolution image 2 | Images 8, 9, 10, 11, 12, 13, and 14 |
| Super-resolution image 3 | Images, 1', 2', 3', 4', 5', 6', and 7' |
| Super-resolution image 4 | Images, 8', 9', 10', 11', 12', 13', and 14' |

As described, in the present example, while the refresh frequency of the super-resolution image is less than the refresh frequency in example 8, there is a benefit in that the direction switching of the interference fringes can be optimized.

Note that in the present example, acquisition of the final image in the round (image 14) may be omitted and the first image of the next round (image 1') may be used as the image 14. With such an arrangement, the number of acquired images N in the round can be reduced by one (N=13).

Example 10 of Continuously Observing Sample 2

Example 10 of the embodiment of continuously observing sample 2 will be described.

In the present example, Section 2.7 of 3D-SIM mode is applied.

Therefore, the images required for refreshing the super-resolution image consist of, among the three wave vectors having a mutually closed relationship, two modulated images having differing phases acquired at one wave vector, two modulated images having differing phases acquired at another wave vector, and four modulated images having differing phases acquired at the remaining wave vector. Accordingly, the number of types of images M required for refreshing the super-resolution image is M=8.

Additionally, the refresh frequency of the super-resolution image is set to "every eight images". That is, L is set so that L=8.

Additionally, the number of images P constituting the image set referenced at the time of refreshing is equal to the number of types of images M required for refreshing. In other words, the number of images P constituting the image set is P=M=8.

Moreover, in the present example, the arrangement of the N images in one round is set as shown in Table 21 so as to fulfill the uniformity condition, the refresh condition, the continuity condition, and the direction condition described above. With the arrangement of Table 21, the number of acquired images N in one round is N=16.

TABLE 21

| Image 1 | Direction 1, phase $\theta1$ modulated image |
| Image 2 | Direction 1, phase $\theta1 + \pi/2$ modulated image |
| Image 3 | Direction 1, phase $\theta1 + \pi$ modulated image |
| Image 4 | Direction 1, phase $\theta1 + 3\pi/2$ modulated image |
| Image 5 | Direction 2, phase $\theta2$ modulated image |
| Image 6 | Direction 2, phase $\theta2 + \pi$ modulated image |
| Image 7 | Direction 3, phase $\theta3$ modulated image |
| Image 8 | Direction 3, phase $\theta3 + \pi$ modulated image |
| Image 9 | Direction 3, phase $\theta3 + 3\pi/2$ modulated image |
| Image 10 | Direction 3, phase $\theta3 + \pi/2$ modulated image |
| Image 11 | Direction 2, phase $\theta2 + 3\pi/2$ modulated image |
| Image 12 | Direction 2, phase $\theta2 + \pi/2$ modulated image |
| Image 13 | Direction 1, phase $\theta1 + 3\pi/2$ modulated image |
| Image 14 | Direction 1, phase $\theta1 + \pi$ modulated image |
| Image 15 | Direction 1, phase $\theta1 + \pi/2$ modulated image |
| Image 16 | Direction 1, phase $\theta1$ modulated image |

Note that the directions in Table 21 represent the direction of the wave vector, the phases represent the phase of the wave vector, and the image numbers represent the acquisition order of the images. Additionally, while the phases $\theta1$, $\theta2$, and $\theta3$ in Table 21 are each optional, it is assumed that direction 1 and direction 2 are directions that are adjacent to each other, direction 2 and direction 3 are directions that are adjacent to each other, but direction 1 and direction 3 are directions that are not adjacent to each other. Direction 2 is, for example a direction rotated 60° from direction 1, and direction 3 is, for example a direction rotated 60° from direction 2.

Moreover, in the present example, the images used in refreshing the super-resolution image are the combinations shown in Table 22.

TABLE 22

| Super-resolution image 1 | Images 1, 2, 3, 4, 5, 6, 7, and 8 |
| Super-resolution image 2 | Images 9, 10, 11, 12, 13, 14, 15, and 16 |
| Super-resolution image 3 | Images 1', 2', 3', 4', 5', 6', 7', and 8' |
| Super-resolution image 4 | Images 9', 10', 11', 12', 13', 14', and 15' |

Note that the super-resolution image numbers in Table 22 represent the generation order of the super-resolution images.

Example 11 of Continuously Observing Sample 2

Example 11 for preventing fading inconsistencies on the sample 2 will be described below.

The present example is a variation of example 10, and therefore only the differences between the present example and example 10 will be described here.

In the present example, the refresh condition is strengthened relative to that used in example 10 and the direction condition is removed.

In order to strengthen the refresh condition, in the present example, the refresh frequency of the super-resolution image is increased to "every images" (L=2).

That is, in the present example, the arrangement of the N images in one round is set as shown in Table 23 so as to fulfill the uniformity condition, the refresh condition (where L=2), and the continuity condition. With the arrangement of Table 23, the number of acquired images N in one round is N=36.

TABLE 23

| Image 1 | Direction 1, phase $\theta1$ modulated image |
| Image 2 | Direction 1, phase $\theta1 + \pi$ modulated image |
| Image 3 | Direction 2, phase $\theta2$ modulated image |
| Image 4 | Direction 2, phase $\theta2 + \pi$ modulated image |
| Image 5 | Direction 3, phase $\theta3$ modulated image |
| Image 6 | Direction 3, phase $\theta3 + \pi$ modulated image |
| Image 7 | Direction 3, phase $\theta3 + \pi/2$ modulated image |
| Image 8 | Direction 3, phase $\theta3 + 3\pi/2$ modulated image |
| Image 9 | Direction 1, phase $\theta1 + \pi/2$ modulated image |
| Image 10 | Direction 1, phase $\theta1 + 3\pi/2$ modulated image |
| Image 11 | Direction 2, phase $\theta2 + \pi/2$ modulated image |
| Image 12 | Direction 2, phase $\theta2 + 3\pi/2$ modulated image |
| Image 13 | Direction 2, phase $\theta2$ modulated image |
| Image 14 | Direction 2, phase $\theta2 + \pi$ modulated image |
| Image 15 | Direction 3, phase $\theta3$ modulated image |
| Image 16 | Direction 3, phase $\theta3 + \pi$ modulated image |
| Image 17 | Direction 1, phase $\theta1$ modulated image |
| Image 18 | Direction 1, phase $\theta1 + \pi$ modulated image |
| Image 19 | Direction 1, phase $\theta1 + \pi/2$ modulated image |
| Image 20 | Direction 1, phase $\theta1 + 3\pi/2$ modulated image |
| Image 21 | Direction 2, phase $\theta2 + \pi/2$ modulated image |
| Image 22 | Direction 2, phase $\theta2 + 3\pi/2$ modulated image |
| Image 23 | Direction 3, phase $\theta3 + \pi/2$ modulated image |
| Image 24 | Direction 3, phase $\theta3 + 3\pi/2$ modulated image |
| Image 25 | Direction 3, phase $\theta3$ modulated image |
| Image 26 | Direction 3, phase $\theta3 + \pi/2$ modulated image |
| Image 27 | Direction 1, phase $\theta1$ modulated image |
| Image 28 | Direction 1, phase $\theta1 + \pi$ modulated image |
| Image 29 | Direction 2, phase $\theta2$ modulated image |
| Image 30 | Direction 2, phase $\theta2 + \pi$ modulated image |
| Image 31 | Direction 2, phase $\theta2 + \pi/2$ modulated image |
| Image 32 | Direction 2, phase $\theta2 + 3\pi/2$ modulated image |
| Image 33 | Direction 3, phase $\theta3 + \pi/2$ modulated image |
| Image 34 | Direction 3, phase $\theta3 + 3\pi/2$ modulated image |
| Image 35 | Direction 1, phase $\theta1 + \pi/2$ modulated image |
| Image 36 | Direction 1, phase $\theta1 + 3\pi/2$ modulated image |

Note that the directions in Table 23 represent the direction of the wave vector, the phases represent the phase of the wave vector, and the image numbers represent the acquisition order of the images. Additionally, phases $\theta1$, $\theta2$, and $\theta3$, and direction 1, direction 2, and direction 3 in Table 23 are each optional. The relationship between direction 1, direction 2, and direction 3 may, for example, be the relationship between the first direction V1, the second direction V2, and the third direction V3 (see FIGS. 2A and 2B).

Moreover, in the present example, the images used in refreshing the super-resolution image are the combinations shown in Table 24.

TABLE 24

| Super-resolution image 1 | Images 1, 2, 3, 4, 5, 6, 7, and 8 |
| Super-resolution image 2 | Images 3, 4, 5, 6, 7, 8, 9, and 10 |
| Super-resolution image 3 | Images 5, 6, 7, 8, 9, 10, 11, and 12 |
| Super-resolution image 4 | Images 7, 8, 9, 10, 11, 12, 13, and 14 |
| Super-resolution image 5 | Images 9, 10, 11, 12, 13, 14, 15, and 16 |
| Super-resolution image 6 | Images 11, 12, 13, 14, 15, 16, 17, and 18 |
| Super-resolution image 7 | Images 13, 14, 15, 16, 17, 18, 19, and 20 |
| Super-resolution image 8 | Images 15, 16, 17, 18, 19, 20, 21, and 22 |
| Super-resolution image 10 | Images 17, 18, 19, 20, 21, 22, 23, and 24 |

As described, in the present example, while the efficiency of direction switching of the interference fringes is lower than in Example 10, there is a benefit in that the refresh frequency of the super-resolution image can be increased.

Example 12 of Continuously Observing Sample 2

Example 12 of the embodiment of continuously observing sample 2 will be described below.

In the present example, Section M of 3D-SIM mode is applied.

Therefore, the images required for refreshing the super-resolution image consist of, among the three wave vectors having a mutually closed relationship, four modulated images having differing phases acquired at one wave vector, four modulated images having differing phases acquired at another wave vector, and four modulated images having differing phases acquired at the remaining wave vector. Accordingly, the number of types of images M required for refreshing the super-resolution image is M=12.

Additionally, the refresh frequency of the super-resolution image is set to "every 12 images". That is, L is set so that L=12.

Additionally, the number of images P constituting the image set referenced at the time of refreshing is equal to the number of types of images M required for refreshing. In other words, the number of images P constituting the image set is P=M=12.

Moreover, in the present example, the arrangement of the N images in one round is set as shown in Table 25 so as to fulfill the uniformity condition, the refresh condition, and the continuity condition described above. With the arrangement of Table 25, the number of acquired images N in one round is N=12.

TABLE 25

| Image 1 | Direction 1, phase θ1 modulated image |
| Image 2 | Direction 1, phase θ1 + π/2 modulated image |
| Image 3 | Direction 1, phase θ1 + π modulated image |
| Image 4 | Direction 1, phase θ1 + 3π/2 modulated image |
| Image 5 | Direction 2, phase θ2 modulated image |
| Image 6 | Direction 2, phase θ2 + π/2 modulated image |
| Image 7 | Direction 2, phase θ2 + π modulated image |
| Image 8 | Direction 2, phase θ2 + 3π/2 modulated image |
| Image 9 | Direction 3, phase θ3 modulated image |
| Image 10 | Direction 3, phase θ3 + π/2 modulated image |
| Image 11 | Direction 3, phase θ3 + π modulated image |
| Image 12 | Direction 3, phase θ3 + 3π/2 modulated image |

Note that the directions in Table 25 represent the direction of the wave vector, the phases represent the phase of the wave vector, and the image numbers represent the acquisition order of the images. Additionally, direction 1, direction 2, direction 3, and phases θ1, θ2, and θ3 in Table 25 are each optional. The relationship between direction 1, direction 2, and direction 3 may for example, be the relationship between the first direction V1, the second direction V2, and the third direction V3 (see FIGS. 2A and 2B).

Moreover, in the present example, the images used in refreshing the super-resolution image are the combinations shown in Table 26.

TABLE 26

| Super-resolution image 1 | Image 1 to Image 12 |
| Super-resolution image 2 | Image 1' to Image 12' |

Note that the super-resolution image numbers in Table 26 represent the generation order of the super-resolution images.

Additionally, in the present example, because the isotropy condition described above is fulfilled, there is a benefit in that the fading state of the sample 2 will be isotropic.

Note that in the preceding explanation, the number of wave vectors used to acquire the required modulated images is set to three and the relationship between the three wave vectors is set to be closed, but the number of wave vectors is not limited and may also be set to three or greater. For example, the number of wave vectors may be set to five and the relationship between these five wave vectors may be a closed relationship, or the number of wave vectors may be set to Q (where Q≥3) and the relationship between the Q wave vectors may be a closed relationship.

<Effects and Benefits of the Embodiment of Continuously Observing Sample 2>

The structured illumination microscope device 1 of the present embodiment comprises: acquisition unit (control device 43) that repeats a series of processing including controlling a combination of a wave vector and phase of fringes that spatially modulates a sample 2 and sequentially acquiring N images related to the sample; and computing unit (image storage/processing device 44) in which processing for demodulating the image of the sample using a required M types of images from an image set of consecutive P images updated upon acquisition of L of the images is performed on each of the image sets.

The M types of images includes the following images.
Q types (Q≥3) of modulated images having a mutually closed relationship between the wave vectors.
One type of modulated image having a wave vector in common with and a phase differing from at least one among the three types of modulated images, or one unmodulated image.

Additionally, the arrangement of the N images fulfills the following conditions.
Uniformity condition: The intensity distribution of the fringes is spatially uniform (or substantially uniform) when accumulated between the N images.
Refresh condition: The image set always includes the M types of images.

According to the structured illumination microscope device of the present embodiment, the super-resolution image is refreshed upon acquisition of L images in the series of processing, and fading inconsistency on the sample in the period from the beginning to the end of the series of processing is eliminated. Therefore, there will be no worsening of the fading, even when the series of processing is repeated multiple times.

Additionally, the number of images P constituting the image set is equal to the number of types of images M required for demodulation.

Additionally, the number of acquired images L corresponding to the frequency of demodulation may be one or two.

Additionally, the number of acquired images L corresponding to the frequency of demodulation need not be equal to the number of types of images M required for demodulation.

Additionally, the arrangement of the N images may fulfill the following condition.
Direction condition: Direction switching of the wave vectors is limited to switching between directions that are adjacent to each other.

Additionally, the arrangement of the N images may fulfill the following condition.

Continuity condition: Among the M types of images required for demodulation, modulated images having a common wave vector are continuous within the image set.

Additionally, the arrangement of the N images may fulfill the following condition in a case where the number of types of the modulated images Q is three.

Isotropy condition: The number of modulated images acquired having a wave vector in common with one among the Q types (where Q=3) of modulated images is equal to the number of modulated images acquired having a wave vector in common with another of the types, and the number of modulated images acquired having a wave vector in common with the remaining type.

The M types of images may include the following images (where M=4).

Q types (Q=3) of modulated images having a mutually closed relationship between the wave vectors.

One type of modulated image having a wave vector in common with and a phase differing from any one among the Q types of modulated images (Q=3).

Additionally, the computing unit, in the spatial frequency spectrum of each of the M types of images (where M=4), may isolate the zero-order modulation component and the ±first-order modulation components of the observed beam, superposed on any three observation points, from each other, on the basis of the 12 observation values related to the three observation points offset from each other by the amount of the wave vector of the Q types of modulated images (Q=3).

Additionally, among the M types of images (where M=4), the difference between the phases of at least two types of the modulated images having a common wave vector may be $\pi$.

The M types of images may include the following images (where M=4).

Q types (Q=3) of modulated images having a mutually closed relationship between the wave vectors.

One unmodulated image

Additionally, the computing unit, in the spatial frequency spectrum of each of the M types of images (where M=4), may isolate the zero-order modulation component and the ±first-order modulation components of the observed beam, superposed on the three observation points, from each other, on the basis of 12 observation values related to any three observation points offset from each other by the amount of the wave vector of the Q types of modulated images (Q=3).

The M types of images may include the following images (where M=7).

Q types (Q=3) of modulated images having a mutually closed relationship between the wave vectors.

One type of modulated image having a wave vector in common with and a phase differing from any one among the Q types of modulated images (Q=3).

One type of modulated image having a wave vector in common with and a phase differing from another among the Q types of modulated images (Q=3), One type of modulated image having a wave vector in common with and a phase differing from the remaining among the Q types of modulated images (Q=3).

One unmodulated image.

Additionally, the computing unit, in the spatial frequency spectrum of each of the M types of images (where M=7), may isolate the ±first-order modulation components of the observed beam, superposed on any three observation points, from each other, on the basis of 21 observation values related to the three observation points offset from each other by the amount of the wave vector of the Q types of modulated images (Q=3); and may isolate the zero-order modulation component and the ±second-order modulation components of the observed beam, superposed on any three observation points, from each other, on the basis of 21 observation values related to the observation points offset from each other by two-times the amount of the wave vector.

Additionally, among the M types of images (where M=7), the difference between the phases of two types of the modulated images acquired at at least one of the wave vectors may be $\pi$.

The M types of images may include the following images (where M=12).

Q types (Q=3) of modulated images having a mutually closed relationship between the wave vectors.

Three types of modulated images having a wave vector in common with and a phase differing from any one among the Q types of modulated images (Q=3).

Three types of modulated images having a wave vector in common with and a phase differing from another among the Q types of modulated images (Q=3).

Three types of modulated images having a wave vector in common with and a phase differing from the remaining among the Q types of modulated images (Q=3).

Additionally, the computing unit, in the spatial frequency spectrum of each of the M types of modulated images (where M=12), may isolate the ±first-order modulation components of the observed beam, superposed on any three observation points, from each other, on the basis of 36 observation values related to the three observation points offset from each other by the amount of the wave vector of the Q types of modulated images (Q=3); and may isolate the zero-order modulation component and the ±second-order modulation components of the observed beam, superposed on any three observation points, from each other, on the basis of 36 observation values related to the three observation points offset from each other by two-times the amount of the wave vector.

The M types of images may include the following images (where M=8).

Q types (Q=3) of modulated images having a mutually closed relationship between the wave vectors.

One type of modulated image having a wave vector in common with and a phase differing from any one among the Q types of modulated images (Q=3).

One type of modulated image having a wave vector in common with and a phase differing from another among the Q types of modulated images (Q=3).

Three types of modulated images having a wave vector in common with and a phase differing from the remaining among the Q types of modulated images (Q=3).

Additionally, the computing unit, in the spatial frequency spectrum of each of the M types of images (where M=8), may isolate the ±first-order modulation components of the observed beam, superposed on any three observation points, from each other, on the basis of 24 observation values related to the three observation points offset from each other by the amount of the wave vector of the Q types of modulated images (Q=3); and may isolate the zero-order modulation component and the ±second-order modulation components of the observed beam, superposed on any three observation points, from each other, on the basis of 24 observation values related to the three observation points offset from each other by two-times the amount of the wave vector.

Additionally, among the M types of images (where M=8), the difference between the phases of four types of the modulated images having a common wave vector may be π/2.

Additionally, the magnitude of the wave vectors between the Q types of modulated images (Q=3) may be common and the direction thereof may be offset 120° from each other.

Note that N, L, P, M, and Q are all integers.

<Additional Notes>

Note that various aspects of the embodiments described above may be combined as appropriate. Moreover, some of the component parts may be removed. Moreover, to the extent permissible by law, all publications and US patent documents related to the devices or the like used in the embodiments and variations as described above are incorporated herein by reference.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illumination microscope device comprising:
   a diffraction grating;
   a projection optical system that projects light from a light source onto an object to be observed via the diffraction grating or bypassing the diffraction grating;
   a control unit that controls a direction and a phase of a pattern of the diffraction grating;
   an image-forming optical system that forms an image of the object to be observed on which the pattern of the diffraction grating is projected;
   an image sensor that generates an image by capturing the image formed by the image-forming optical system; and
   computing unit that generates a super-resolution image of the object to be observed on the basis of at least one unmodulated image generated by the image sensor and an image generated by the image sensor on the basis of patterns in at least three directions of the diffraction grating; and
   the control unit being configured to perform control such that a pattern in at least one direction of the diffraction grating is radiated uniformly on the object to be observed when a plurality of the super-resolution images is generated.

2. The structured illumination microscope device according to claim 1, wherein
   each time the image sensor generates a new image, the computing unit uses the new image in place of an oldest image to generate the super-resolution image.

3. A structured illumination microscope device, comprising:
   a diffraction grating;
   a projection optical system that projects light from a light source onto an object to be observed via the diffraction grating or bypassing the diffraction grating;
   a control unit that controls a direction and a phase of a pattern of the diffraction grating;
   an image-forming optical system that forms an image of the object to be observed on which the pattern of the diffraction grating is projected;
   an image sensor that generates an image by capturing the image formed by the image-forming optical system; and
   computing unit that generates a super-resolution image of the object to be observed on the basis of an image generated by the image sensor on the basis of patterns in at least three directions of the diffraction grating; and
   the control unit being configured to perform control such that, in a case where a pattern in at least one direction of the diffraction grating is not radiated uniformly on the object to be observed when the super-resolution image is generated, a pattern in at least one direction of the diffraction grating is radiated uniformly on the object to be observed when a plurality of the super-resolution images is generated.

4. The structured illumination microscope device according to claim 3, wherein
   each time the image sensor generates a new image, the computing unit uses the new image in place of an oldest image to generate the super-resolution image.

5. A structured illumination microscope device comprising:
   a diffraction grating;
   a projection optical system that projects light from a light source onto an object to be observed via the diffraction grating or bypassing the diffraction grating;
   a control unit that controls a direction and a phase of a pattern of the diffraction grating;
   an image-forming optical system that forms an image of the object to be observed on which the pattern of the diffraction grating is projected; and
   an image sensor that generates an image by capturing the image formed by the image-forming optical system; and
   computing unit that generates a super-resolution image of the object to be observed on the basis of at least one unmodulated image generated by the image sensor and an image generated by the image sensor on the basis of patterns in at least three directions of the diffraction grating; and
   the control unit being configured to change the phase of a pattern in at least one direction of the diffraction grating when a plurality of the super-resolution images is generated.

6. A structured illumination microscope device comprising:
   a diffraction grating;
   a projection optical system that projects light from a light source onto an object to be observed via the diffraction grating or bypassing the diffraction grating;
   a control unit that controls a direction and a phase of a pattern of the diffraction grating;
   an image-forming optical system that forms an image of the object to be observed on which the pattern of the diffraction grating is projected; and
   an image sensor that generates an image by capturing the image formed by the image-forming optical system; and
   computing unit that generates a super-resolution image of the object to be observed on the basis of an image generated by the image sensor on the basis of patterns in at least three directions of the diffraction grating; and
   in a case where a pattern in at least one direction of the diffraction grating is not radiated uniformly on the object to be observed when the super-resolution image is generated, the control unit being configured to change the phase of a pattern in at least one direction of the diffraction grating when a plurality of the super-resolution images is generated.

* * * * *